US012788713B2

(12) United States Patent
Patel et al.

(10) Patent No.: US 12,788,713 B2
(45) Date of Patent: Nov. 10, 2026

(54) IMPLANTABLE DEVICES FOR DRUG DELIVERY WITH REDUCED BURST RELEASE

(71) Applicant: REACX PHARMACEUTICALS, INC., South San Francisco, CA (US)

(72) Inventors: Rajesh A. Patel, Redwood City, CA (US); Sunil Sreedharan, South San Francisco, CA (US); Sunil R. Bhonsle, Oakland, CA (US)

(73) Assignee: ReacX Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 18/236,721

(22) Filed: Aug. 22, 2023

(65) Prior Publication Data

US 2024/0189224 A1 Jun. 13, 2024

Related U.S. Application Data

(63) Continuation of application No. 16/338,962, filed as application No. PCT/US2017/055432 on Oct. 5, 2017, now abandoned.

(60) Provisional application No. 62/404,643, filed on Oct. 5, 2016.

(51) Int. Cl.

| | |
|---|---|
| ***A61K 9/00*** | (2006.01) |
| ***A61K 9/14*** | (2006.01) |
| ***A61K 9/48*** | (2006.01) |
| ***A61K 31/197*** | (2006.01) |
| ***A61K 31/4045*** | (2006.01) |
| ***A61K 31/4458*** | (2006.01) |
| ***A61K 31/485*** | (2006.01) |
| ***A61K 31/506*** | (2006.01) |
| ***A61K 38/26*** | (2006.01) |
| *B29C 48/06* | (2019.01) |
| *B29C 48/21* | (2019.01) |
| *B29K 1/00* | (2006.01) |
| *B29K 23/00* | (2006.01) |
| *B29K 105/00* | (2006.01) |
| *B29L 31/00* | (2006.01) |

(52) U.S. Cl.

CPC .......... *A61K 9/0024* (2013.01); *A61K 9/4808* (2013.01); *A61K 9/4816* (2013.01); *A61K 9/4833* (2013.01); *A61K 31/197* (2013.01); *A61K 31/4045* (2013.01); *A61K 31/4458* (2013.01); *A61K 31/485* (2013.01); *A61K 31/506* (2013.01); *A61K 38/26* (2013.01); *B29C 48/06* (2019.02); *B29C 48/21* (2019.02); *B29K 2001/08* (2013.01); *B29K 2023/083* (2013.01); *B29K 2105/0035* (2013.01); *B29K 2995/006* (2013.01); *B29L 2031/753* (2013.01)

(58) Field of Classification Search

CPC ............................ A61K 9/0024; A61K 9/4816

See application file for complete search history.

(56) References Cited

U.S. PATENT DOCUMENTS

| | | | | |
|---|---|---|---|---|
| 4,666,704 A | | 5/1987 | Shalati | |
| 4,673,565 A | * | 6/1987 | Di Luccio | A61K 9/70 424/443 |
| 5,683,719 A | | 11/1997 | Newton | |
| 5,756,115 A | | 5/1998 | Moo-Young | |
| 5,851,547 A | * | 12/1998 | Fujioka | A61K 9/0092 424/424 |
| 6,126,956 A | | 10/2000 | Grossman | |
| 6,413,993 B1 | * | 7/2002 | Chulay | A61K 31/47 514/565 |
| 8,263,108 B2 | | 9/2012 | Gibson et al. | |
| 2007/0275031 A1 | | 11/2007 | Patel et al. | |
| 2008/0095849 A1 | * | 4/2008 | Wu | A61P 27/16 514/6.9 |
| 2009/0030399 A1 | * | 1/2009 | Raiszadeh | A61F 2/441 604/151 |
| 2009/0155326 A1 | | 6/2009 | Mack et al. | |
| 2013/0209539 A1 | | 8/2013 | Loxley | |
| 2013/0344125 A1 | | 12/2013 | Govender et al. | |
| 2016/0129157 A1 | | 5/2016 | Brooks | |

FOREIGN PATENT DOCUMENTS

| | | |
|---|---|---|
| CA | 2451187 C | 1/2003 |
| WO | 2016/097297 A1 | 6/2016 |

OTHER PUBLICATIONS

Polysciences, Poly(ethylene/vinyl aceate) [60:40 (wt)], obtained online at: https://www.polysciences.com/default/polyethylenevinyl-acetate-6040-wt, downloaded on Jul. 24, 2024. (Year: 2024).*

Prasertmanakit et al., Ethyl cellulose microcapsules for protecting and controlled release of folic acid. AAPS PharmSciTech. 2009; 10(4):1104-12. doi: 10.1208/s12249-009-9305-3. Epub Sep. 10, 2009. PMID: 19763838; PMCID: PMC2799571. (Year: 2009).*

(Continued)

*Primary Examiner* — Abigail Vanhorn

(74) *Attorney, Agent, or Firm* — Wiggin and Dana LLP

(57) ABSTRACT

The invention provides implantable drug delivery devices comprising a core comprising a polymer (or polymer blend) and one or more drugs or pharmaceutical substances, and an outer shell comprising a polymer (or polymer blend) and one or more porogen materials. The invention reduces burst release of drug. Pharmaceuticals such as triiodothyronine (T3) or ropinirole can be delivered by the devices.

32 Claims, 19 Drawing Sheets

(56) References Cited

OTHER PUBLICATIONS

PubChem, ethyl cellulose, obtained online at: https://pubchem.ncbi.nlm.nih.gov/compound/Ethyl-cellulose, downloaded on Jul. 24, 2024. (Year: 2024).*
Girija, B. G., et al. "Mechanical and thermal properties of EVA blended with biodegradable ethyl cellulose." Journal of applied polymer science 116.2 (2010): 1044-1056. (Year: 2010).*
Almeida et al., Sustained release from hot-melt extruded matrices based on ethylene vinyl acetate and polyethylene oxide, European Journal of Pharmaceutics and Biopharmaceutics, vol. 82, Issue 3, pp. 526-533, ISSN 0939-6411, https://doi.org/10.1016/j.ejpb.2012.08.008. (Year: 2012).*
Decision to Grant a European Patent pursuant to Article 97(1) Epc, Ep Application No. 1785227.5, Mailed May 11, 2023.
Response to Communication pursuant to Article 94(3) EPC dated Sep. 21, 2021 and Experimental Annex, EP Application No. 1785227.5, Submitted to the EPO on Mar. 31, 2022.
Communication pursuant to Article 94(3) EPC and Annex to the Communication, EP Application No. 1785227.5, Mailed Sep. 21, 2021.
Supplementary European Search Report and Opinion, EP Application No. 17859227.5, Corr EP Patent No. 3522825, mailed May 19, 2020.
International Search Report and Opinion, International Application No. PCT/2017/055432, mailed Jan. 2, 2018.
Klee, G.G. "Clinical usage recommendations and analytical performance goals for total and free triiodothyronine measurements," 1996, Clinical Chemistry, 42:1, pp. 155-159.
Almeida, A. et al. "Ethylene vinyl acetate as matrix for oral sustained release dosage forms produced via hot-melt extrusion," 2011, European Journal of Pharmaceutics and Biopharmaceutics, 77, pp. 297-305.
Sperling L.E. et al. "Advantages and challenges offered by biofunctional core-shell fiber systems for tissue engineering and drug delivery" 2016, Drug Discovery Today, 21:8, pp. 1243-1256.
Liao, I.C. et al. "Aligned core-shell nanofibers delivering bioactive proteins" 2006, Future Medicine, 1:4, pp. 465-471.

* cited by examiner

IMPLANTABLE DEVICES FOR DRUG DELIVERY WITH REDUCED BURST RELEASE

CROSS REFERENCE TO RELATED APPLICATIONS

This patent application is a continuation application of U.S. patent application Ser. No. 16/338,962, having an International Filing Date of Oct. 5, 2017, which is a national stage application under 35 U.S.C. § 371 of International Application No. PCT/US2017/055432 having an International Filing Date of Oct. 5, 2017, and claims priority benefit of U.S. Provisional Patent Application No. 62/404,643 filed Oct. 5, 2016. The entire contents of those applications are hereby incorporated by reference herein.

TECHNICAL FIELD

The invention provides devices which can be implanted into a patient for release of pharmaceutical substances, such as triiodothyronine, over long periods of time, with reduced, minimal, or no burst release.

BACKGROUND OF THE INVENTION

Many patients require long-term, regular dosing with drugs or pharmaceutical substances. Effective treatment often necessitates the ingestion of one or more tablets per day for extended periods of time. For example, patients who undergo thyroidectomy, a common treatment for thyroid cancer, must take oral thyroxine tablets for the rest of their lifetime. Typically, patients take levothyroxine ($T_4$), which is converted in vivo into triiodothyronine ($T_3$). Both $T_4$ and $T_3$ regulate a wide variety of metabolic pathways in humans, including the basal metabolic rate.

Several problems can arise during long-term administration of drugs taken orally or by other routes requiring frequent administration. Compliance with an extended dosing regimen can often be inconvenient or difficult. For example, patients with impaired cognitive function (due to Alzheimer's disease or other disorders) may not be able to self-administer drugs reliably, requiring a caregiver to ensure that medications are taken properly. Furthermore, enteral drug delivery is sometimes poorly tolerated or prohibited in patients with particular indications. Frequent or periodic administration, such as would occur with daily oral and sublingual delivery, can result in blood concentrations of drug peaking quickly after initial administration, then dropping steeply before the next administration.

Implantable devices used for drug delivery can overcome several problems with oral, sublingual, or intravenous administration of drugs. These devices can produce long-term, continuous delivery of drugs, ensure compliance independent of the patient, maintain stable blood levels of medication, and reduce the likelihood of accidental use, abuse, or diversion for sale. Continuous release of a compound in vivo over an extended duration may be achieved via implantation of a device containing the compound encapsulated in a polymeric matrix. Examples of implantable polymeric devices for continuous drug release are described in, e.g., U.S. Pat. Nos. 4,883,666; 5,114,719; and 5,601,835. Patel et al. U.S. Patent Application Publication Nos. 2004/0033250, 2007/0275031, and 2008/0026031, and Kleppner et al. 2006 J. Pharm. Pharmacol. 58:295-302 describe an implantable device comprising buprenorphine blended with ethylene vinyl acetate (EVA copolymer). Patel et al. U.S. Patent Application Publication No. 2005/0031668 describes an implantable polymeric device for sustained release of nalmefene. Patel et al. U.S. Patent Application Publication No. 2005/0031667 describes an implantable polymeric device for sustained release of dopamine agonists. Additional drug delivery devices include stents coated with compositions comprising drugs. Various devices and coatings are described in U.S. Pat. No. 6,506,437 to Harish; U.S. Pat. No. 7,364,748 to Claude and U.S. Pat. No. 7,384,660 to Hossainy. U.S. Pat. No. 3,625,214 describes a drug-delivery device for prolonged drug delivery, fabricated in a spiral or "jellyroll" fashion. U.S. Pat. No. 3,926,188 describes a three-layer laminate drug dispenser comprising a core lamina of a crystalline drug of low water solubility dispersed in a polymer matrix, interposed between outer laminas made of a drug release rate controlling polymer. U.S. Pat. No. 5,683,719 describes a controlled release composition comprising an extruded core of active material and excipients, the core being coated in a water insoluble coating.

One difficulty encountered with virtually all sustained drug formulations, including implants, is burst release. Burst release is a high release of drug when the formulation is first administered which is higher than the desired release rate, and which can cause deleterious pharmacological effects resulting from excessive levels of drug. This is particularly undesirable for systems, such as implants, that release thyroid hormones, as dangerous cardiac complications may occur. There is thus a need to reduce or eliminate burst release in controlled-release systems for delivery of pharmaceutical substances, including thyroid hormones such as $T_3$.

BRIEF SUMMARY OF THE INVENTION

The invention provides implantable drug delivery devices comprising a core comprising a polymer (or polymer blend) and one or more drugs or pharmaceutical substances, and an outer shell comprising a polymer (or polymer blend) and one or more porogen materials. The shell can optionally additionally comprise one or more drugs or pharmaceutical substances. Surrounding the drug-containing core with a porogen-containing shell can reduce the burst release often observed with sustained release formulations. Use of a porogen material having a narrow size distribution, and the resulting narrow size distribution of the pores left in the shell after removal of the porogen, also allows better control and tuning of the release rate of the drug from the core.

In some embodiments, the invention provides an implantable device for delivery of a pharmaceutical substance comprising a core comprising a first polymeric material and a core pharmaceutical substance; and a shell comprising a second polymeric material and a porogen material. The shell can lack a pharmaceutical substance, or alternatively the shell can further comprise a pharmaceutical substance (referred to as a "shell pharmaceutical substance"). The shell can comprise about 1 wt % to about 80 wt % porogen material. In some embodiments, the porogen material comprises spherical particles and at least about 90% of the spherical particles have a diameter between about 1 micrometer and about 50 micrometers. In some embodiments, the porogen material comprises spherical particles with a mean diameter between about 1 micrometer and about 50 micrometers. In some embodiments, the porogen material comprises spherical particles and at least about 90% of the spherical particles have a diameter that varies by 10% or less from a mean diameter.

The porogen material can comprise a bioerodible material. The porogen material can comprise a non-bioerodible material. The porogen material can comprise a material selected from the group consisting of an alkyl cellulose, a hydroxyalkyl cellulose, ethylcellulose, methylcellulose, hydroxymethylcellulose, a fatty acid, stearic acid, palmitic acid, myristic acid, linoleic acid, a biocompatible salt, sodium chloride, calcium chloride, and sodium phosphate; in some embodiments, the porogen material comprises ethyl cellulose. In some embodiments, the porogen material dissolves or dissociates from the shell upon washing the implantable device.

The first polymeric material or the second polymeric material can comprise a bioerodible material. The first polymeric material or the second polymeric material can comprise a non-bioerodible material. The first polymeric material can comprise one or more materials selected from the group consisting of poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

The second polymeric material can comprise one or more materials selected from the group consisting of poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly (trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

The first polymeric material can comprise ethylene-vinyl acetate. The second polymeric material can comprise ethylene-vinyl acetate. In one embodiment, both the first polymeric material and the second polymeric material comprise ethylene-vinyl acetate The implantable device can be rod-shaped. In some embodiments, the implantable device has a diameter of about 1 mm to about 8 mm. In some embodiments, the implantable device has a length of about 10 mm to about 80 mm. In some embodiments, the implantable device is capped at one end of the implantable device. In some embodiments, the implantable device is capped at both ends of the implantable device.

The core pharmaceutical substance can comprise one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, atovaquone, proguanil, a combination of atovaquone and proguanil, and nalmefene. In some embodiments, the core pharmaceutical substance comprises triiodothyronine. In some embodiments, the core pharmaceutical substance comprises ropinirole. The core pharmaceutical substance can comprise about 1 wt % to about 80 wt % of the core.

The shell pharmaceutical substance can comprise one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, atovaquone, proguanil, a combination of atovaquone and proguanil, and nalmefene. In some embodiments, the shell pharmaceutical substance comprises triiodothyronine. In some embodiments, the shell pharmaceutical substance comprises ropinirole. The shell pharmaceutical substance can comprise about 1 wt % to about 40 wt % of the shell.

The core pharmaceutical substance and the shell pharmaceutical substance (when present) can be the same pharmaceutical substance, such as triiodothyronine or ropinirole. The core pharmaceutical substance and the shell pharmaceutical substance (when present) can be different pharmaceutical substances.

In some embodiments, the implantable device further comprises a reinforcing member inside the core.

The invention further provides methods of forming the implantable device, comprising extruding a first composition to form a core, the first composition comprising a first polymeric material and a core pharmaceutical substance; and coating the core with second composition to form a shell, the second composition comprising a second polymeric material and a porogen material. The first composition can be formed by combining the first polymeric material with the core pharmaceutical substance. The second composition can be formed by combining the second polymeric material with the porogen material.

The invention further provides methods of forming an implantable device comprising co-extruding a first composition and a second composition, where the first composition is extruded to form a core, the first composition comprising a first polymeric material and a core pharmaceutical substance; and the co-extruded second composition forming a shell around the core, the second composition comprising a second polymeric material and a porogen material. The first composition can be formed by combining the first polymeric material with the core pharmaceutical substance. The second composition can be formed by combining the second polymeric material with the porogen material.

In some embodiments of the methods, the method further comprises washing the implantable device. The implantable device can be washed with ethanol, water, or a mixture of ethanol and water. Washing the device can dissolve the porogen material, or dissociate the porogen material, from the implantable device to form a plurality of pores in the shell.

In any of the implants or methods disclosed herein, the second composition can be a non-medicated material, or the second composition can further comprise a shell pharmaceutical substance.

In any of the implants or methods disclosed herein, the second composition can comprise about 1 wt % to about 40 wt % porogen material. In some embodiments, the porogen material comprises spherical particles and at least about 90% of the spherical particles have a diameter between about 1 micrometer and about 50 micrometers. In some embodiments, the porogen material comprises spherical particles with a mean diameter between about 1 micrometer and about 50 micrometers. In some embodiments, the porogen material comprises spherical particles and at least about 90% of the spherical particles have a diameter that varies by 10% or less from a mean diameter.

In any of the implants or methods disclosed herein, the porogen material comprises particles and the longest dimension of at least about 90% of the particles is between about 1 micrometer and about 50 micrometers. In some embodiments, the porogen material comprises particles and the average longest dimension of the particles is between about 1 micrometer and about 50 micrometers. In some embodiments, the porogen material comprises particles and the longest dimension of at least about 90% of the particles varies by 10% or less from the average longest dimension of the particles.

In any of the implants or methods disclosed herein, the porogen material comprises particles and the mean dimension of at least about 90% of the particles is between about 1 micrometer and about 50 micrometers, where the mean dimension of the particles is the mean of the longest dimension of the particles and the shortest dimension of the particles. In some embodiments, the porogen material comprises particles and the mean dimension of the particles is between about 1 micrometer and about 50 micrometers. In some embodiments, the porogen material comprises particles and the mean dimension of at least about 90% of the particles varies by 10% or less from the average of the mean dimension of the particles.

In any of the implants or methods disclosed herein, the porogen material can comprise a bioerodible material, or the porogen material can comprise a non-bioerodible material. The porogen can comprise a material selected from the group consisting of an alkyl cellulose, a hydroxyalkyl cellulose, ethylcellulose, methylcellulose, hydroxymethylcellulose, a fatty acid, stearic acid, palmitic acid, myristic acid, linoleic acid, a biocompatible salt, sodium chloride, calcium chloride, and sodium phosphate. The porogen material can comprise ethyl cellulose.

In any of the implants or methods disclosed herein, the first polymeric material or the second polymeric material can comprise a bioerodible material. In any of the implants or methods disclosed herein, the first polymeric material or the second polymeric material can comprise a non-bioerodible material.

In any of the implants or methods disclosed herein, the first polymeric material can comprise one or more materials selected from the group consisting of poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

In any of the implants or methods disclosed herein, the second polymeric material can comprise one or more materials selected from the group consisting of polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

In any of the implants or methods disclosed herein, the first polymeric material can comprise ethylene-vinyl acetate. In any of the implants or methods disclosed herein, the second polymeric material can comprise ethylene-vinyl acetate. In any of the implants or methods disclosed herein, first polymeric material can comprise ethylene-vinyl acetate and the second polymeric material can comprise ethylene-vinyl acetate.

In any of the implants or methods disclosed herein, the implantable device can be rod-shaped. In any of the implants or methods disclosed herein, the implantable device can have a diameter of about 1 mm to about 8 mm. In any of the implants or methods disclosed herein, the implantable device can have a length of about 10 mm to about 80 mm.

Any of the implants or methods disclosed herein can further comprise capping the implantable device at one end of the implantable device. Any of the implants or methods disclosed herein can further comprise capping the implantable device at both ends of the implantable device.

In any of the implants or methods disclosed herein, the core pharmaceutical substance can comprise one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, atovaquone, proguanil, a combination of atovaquone and proguanil, and nalmefene. In any of the implants or methods disclosed herein, the core pharmaceutical substance can comprise triiodothyronine. In any of the implants or methods disclosed herein, the core pharmaceutical substance can comprise ropinirole. The core pharmaceutical substance can comprise about 1 wt % to about 80 wt % of the first composition.

In any of the implants or methods disclosed herein, the shell pharmaceutical substance can comprise one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, atovaquone, proguanil, a combination of atovaquone and proguanil, and nalmefene. In any of the implants or methods disclosed herein, the shell pharmaceutical substance can comprise triiodothyronine. In any of the implants or methods disclosed herein, the shell pharmaceutical substance can comprise ropinirole. The shell pharmaceutical substance can comprise about 1 wt % to about 40 wt % of the second composition.

In some embodiments, the invention provides methods of treating a disease in a subject, comprising implanting into the subject any of the implantable devices disclosed herein. The disease can be hypothyroidism, Parkinson's disease, restless leg syndrome (RLS), HIV infection, retroviral infection, pulmonary arterial hypertension, attention deficit/hyperactivity disorder, type 2 diabetes, metabolic syndrome, hyperlipidemia, obesity, malaria, alcoholism, or alcohol addiction.

In some embodiments, the invention provides any of the implantable devices disclosed herein for use in the treatment of a disease. The disease can be hypothyroidism, Parkinson's disease, restless leg syndrome (RLS), HIV infection, retroviral infection, pulmonary arterial hypertension, attention deficit/hyperactivity disorder, type 2 diabetes, metabolic syndrome, hyperlipidemia, obesity, malaria, alcoholism, or alcohol addiction.

In some embodiments, the invention provides for use of any of the implantable devices disclosed herein for treatment of a disease. The disease can be hypothyroidism, Parkinson's disease, restless leg syndrome (RLS), HIV infection, retroviral infection, pulmonary arterial hypertension, attention deficit/hyperactivity disorder, type 2 diabetes, metabolic syndrome, hyperlipidemia, obesity, malaria, alcoholism, or alcohol addiction.

In some embodiments, the invention provides for use of L-thyroxine ($T_4$), L-triiodothyronine ($T_3$), or a combination of L-thyroxine ($T_4$) and L-triiodothyronine ($T_3$) for the manufacture of any of the implantable devices described herein for the treatment of hypothyroidism, metabolic syndrome, hyperlipidemia, or obesity; use of ropinirole for the manufacture of any of the implantable devices described herein for the treatment of Parkinson's disease or restless leg syndrome; use of tenofovir, emtricitabine, or a combination of tenofovir and emtricitabine for the manufacture of any of the implantable devices described herein for the treatment of HIV infection, retroviral infection, or prophylaxis against HIV infection or retroviral infection; use of bosentan for the manufacture of any of the implantable devices described herein for the treatment of pulmonary arterial hypertension; use of methylphenidate for the manufacture of any of the implantable devices described herein for the treatment of attention deficit/hyperactivity disorder; use of liraglutide for the manufacture of any of the implantable devices described herein for the treatment of type 2 diabetes or obesity; use of doxycycline, atovaquone, proguanil, or a combination of atovaquone and proguanil for the manufacture of any of the implantable devices described herein for the treatment of malaria, or for prophylaxis against malaria; or use of nalmefene for the manufacture of any of the implantable devices described herein for the treatment of alcoholism or alcohol addiction.

In some embodiments, the invention provides methods of providing pre-exposure prophylaxis of HIV or prophylaxis of retroviral acquisition, comprising implanting into the subject any of the implantable devices disclosed herein.

The implantable device can release an average of about 10 μg to about 150 μg of the core pharmaceutical substance per day for the first 30 days when implanted in the subject. The implantable device can release the core pharmaceutical substance when implanted in the subject with a daily variance of less than about 10% from the daily average release for the first 30 days.

The implantable device, when implanted in a subject, can release the core pharmaceutical substance with an initial burst at least 50% lower than the initial burst from a comparison implant without the shell. The initial burst period for comparison can be the first hour after implantation, the first six hours after implantation, the first 12 hours after implantation, the first 24 hours after implantation, the first 48 hours after implantation, the first three days after implantation, the first four days after implantation, the first five days after implantation, the first six days after implantation, the first seven days after implantation, the first eight days after implantation, the first nine days after implantation, or the first ten days after implantation. In one embodiment, a comparison implant without the shell is an implant which has only the medicated core of the core-shell implant, and no shell. Thus, for example, in FIG. 1, a comparison implant without the shell would simply have the outer shell removed. In another embodiment, a comparison implant without the shell is an implant where, instead of having a core and a shell, the entire comparison implant is made of the material that forms the core with the same dimensions as the core-shell implant. Thus, for example, in FIG. 1, a comparison implant without the shell would have the outer shell replaced with additional core material containing core pharmaceutical substance, such that the comparison implant has the same dimensions as the implant of the invention, but is uniformly made of core material, including core pharmaceutical substance.

In any of the embodiments described herein, the core pharmaceutical substance can be present in the form of a salt, solvate, or hydrate of the active substance.

In another aspect, the implantable device provides a steady-state level, an approximately constant level, or an essentially constant level of pharmaceutical substance or drug in the blood of the patient.

DETAILED DESCRIPTION OF THE INVENTION

Figure 1:
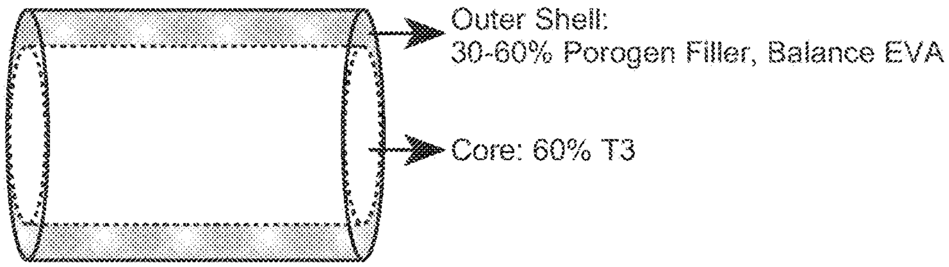
FIG. 1 shows a drawing of one embodiment of an implant of the invention, with about 30% to about 60% porogen filler in the outer shell (the balance of the shell is made of ethylene-vinyl acetate) and about 60% $T_3$ in the core (the balance of the core is made of ethylene-vinyl acetate). The drawing is not to scale.

The invention provides implantable devices for long-term sustained drug delivery. In one embodiment, the devices have reduced burst release upon implantation. The devices comprise:

1) a core comprising a polymer (or mixture of polymers) blended with a drug or pharmaceutical substance (or multiple drugs or pharmaceutical substances), and
2) a shell comprising a polymer (or mixture of polymers) blended with a porogen. The shell optionally also comprises a drug or pharmaceutical substance (or multiple drugs or pharmaceutical substances).

In one embodiment, the porogen is included in the device when implanted into a patient. After implantation into the patient, the porogen in the shell dissolves, leaving pores in the shell polymer. Interstitial fluid can then access the core, resulting in elution of drug into the interstitial fluid and eventually into the systemic circulation.

In another embodiment, the porogen is removed from the device prior to implantation. After implantation into the patient, interstitial fluid can access the core, resulting in dissolution of drug and diffusion through the resulting pores into the interstitial fluid and eventually into the systemic circulation The invention also provides methods for providing sustained drug release and for treating diseases and disorders using the devices of the invention, and kits useful in the methods of the invention.

Definitions and General Descriptions

"Drug" and "pharmaceutical substance" are equivalent terms and are used interchangeably, and encompasses any substance intended for therapeutic, diagnostic, or nutritional use in a patient, individual, or subject in need thereof.

"Drugs" and "pharmaceutical substance" include, but are not limited to, diagnostic agents, therapeutic agents, hormones, nutrients, vitamins, and minerals.

A porogen is a first material which is embedded or mixed into a second material, which can be removed (for example, by dissolution, diffusion, or degradation) from the second material. The removal of the porogen results in the creation of pores in the second material.

"Biocompatible," when used to describe a material or system, indicates that the material or system does not provoke an adverse reaction, or causes only minimal, tolerable adverse reactions, when in contact with an organism, such as a human.

A "patient," "individual," or "subject" refers to a mammal, preferably a human, an agricultural animal such as a cow, pig, goat, or sheep, or a domestic animal such as a dog or cat. In a preferred embodiment, a patient, individual, or subject is a human.

"Treating" a disease or disorder with the devices and methods disclosed herein is defined as administering one or more of the devices disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the devices and methods disclosed herein is defined as administering one or more of the devices disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The devices and methods of the invention can then be used to treat asymptomatic patients at risk of developing the clinical symptoms of the disease or disorder, in order to suppress the appearance of any adverse symptoms.

"Therapeutic use" of the devices disclosed herein is defined as using one or more of the devices disclosed herein to treat a disease or disorder, as defined above. A "therapeutically effective amount" of a drug or a therapeutic agent is an amount of the drug or agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the devices disclosed herein is defined as using one or more of the devices disclosed herein to suppress a disease or disorder, as defined above. A "prophylactically effective amount" of a drug or therapeutic agent is an amount of the drug or agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

"Blood level" as used herein refers to the concentration of a drug, therapeutic agent, hormone, metabolite, or other substance in the blood of a subject. A blood level can be measured in whole blood, blood serum, or blood plasma, as per standard clinical laboratory practice for the substance to be assayed.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a device, composition, or system is described as "consisting essentially of" the listed elements, the device, composition, or system contains the elements expressly listed, and may contain other elements which do not materially affect the condition being treated (for compositions for treating conditions), or the properties of the described device or system. However, the device, composition, or system either does not contain any other elements which do materially affect the condition being treated other than those elements expressly listed (for compositions for treating systems) or does not contain any other elements which do materially affect the properties of the device or system; or, if the device, composition, or system does contain extra elements other than those listed which may materially affect the condition being treated or the properties of the system, the device, composition or system does not contain a sufficient concentration or amount of those extra elements to materially affect the condition being treated by the composition or the properties of the device or system. When a method is described as "consisting essentially of" the listed steps, the method contains the steps listed, and may contain other steps that do not materially affect the condition being treated by the method or the properties of the device or system produced by or used by the method, but the method does not contain any other steps which materially affect the condition being treated by the method or the device or system produced or used other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

Device Structure and Manufacture

Physical Parameters of Devices of the Invention

In some embodiments the devices of the invention are rod-shaped or generally rod-shaped, and are about 0.5 cm to 10 cm in length, such as from about 1 cm to about 6 cm in length, or from about 1 cm to about 5 cm in length, or about 1 cm to about 4 cm in length, or about 1 cm to 3 cm in length, or about 1.5 cm to 3.5 cm in length, or about 2 cm to 4 cm in length, or about 2 cm to about 3 cm in length, or about 2 cm to about 5 cm in length, or about 2 cm to about 6 cm in length, or about 3 cm to about 5 cm in length, or about 3 cm to about 6 cm in length, or about 4 cm to about 5 cm in length, or about 4 cm to about 6 cm in length, or about 2.6 cm in length. In some embodiments, the devices are rod-shaped or generally rod-shaped, and are about 3 cm to about 5 cm in length, or about 3.5 cm to about 4.5 cm, or about 4 cm. In some embodiments, the devices are rod-shaped or generally rod-shaped, and are about 5 cm to about 7 cm in length, or about 5.5 cm to about 6.5 cm, or about 6 cm.

In one embodiment, the devices are rod-shaped or generally rod-shaped, and are about 1 to about 3 mm in diameter, referring to the overall diameter of the device (that is, including both core and shell). In some embodiments, the devices are rod-shaped or generally rod-shaped, and comprise dimensions of about 0.5 to about 7 mm in diameter, or about 2 to about 5 mm in diameter, or about 2 to about 3 mm in diameter, or about 2.4 mm in diameter, or about 3 mm in diameter. In some embodiments, the devices are rod-shaped or generally rod-shaped, and comprise dimensions of about 2.4 mm in total diameter and about 2.6 cm in total length.

Figure 1A:
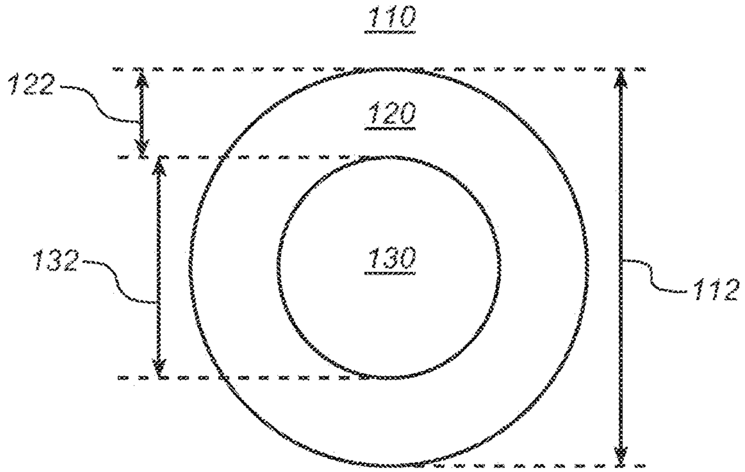
FIG. 1A shows a drawing of a cross-section 110 of an implant of the invention. The drawing is not to scale.

The core and shell can vary independently in thickness. FIG. 1A shows a cross section 110 of one embodiment of an implant with a shell 120 surrounding a core 130. The diameter of the core is indicated by the arrow labeled 132, while the thickness of the shell is indicated by the arrow labeled 122. It should be noted that the overall diameter of the implant device, indicated by the arrow labeled 112, is the diameter of the core 132 plus twice the thickness of the shell 122. In one embodiment, the core independently has a diameter between about 0.25 mm to about 6.75 mm and the shell independently has a thickness between about 0.125 mm to about 3.375 mm, with the proviso that the sum of the diameter of the core and twice the thickness of the shell is less than or equal to about 7 mm (that is, the total diameter of the implantable device is less than or equal to about 7 mm). In one embodiment, the core independently has a diameter between about 0.25 mm to about 4 mm and the shell independently has a thickness between about 0.125 mm to about 2 mm, with the proviso that the sum of the diameter of the core and twice the thickness of the shell is less than or equal to about 7 mm. In one embodiment, the core independently has a diameter between about 1 mm to about 4 mm and the shell independently has a thickness between about 0.125 mm to about 2 mm, with the proviso that the sum of the diameter of the core and twice the thickness of the shell is less than or equal to about 7 mm. In one embodiment, the core independently has a diameter between about 2 mm to about 4 mm and the shell independently has a thickness between about 0.125 mm to about 0.625 mm, with the proviso that the sum of the diameter of the core and twice the thickness of the shell is less than or equal to about 7 mm (in this embodiment, the sum of the diameter of the core and twice the thickness of the shell cannot exceed about 5.25 mm). In a preferred embodiment, the core independently has a diameter of about 2.5 mm to about 3 mm, such as 2.75 mm, and the shell independently has a thickness of about 0.3 mm to about 0.5 mm, such as about 0.375 mm. (In the embodiment where the core has a diameter of 2.75 mm and the shell has a thickness of about 0.375 mm, the total diameter of the implant is about $\{2.75\ \text{mm}+(2\times0.375\ \text{mm})\}=3.5$ mm.)

For rod-shaped devices, a reinforcing member can be incorporated into the core. Such a reinforcing member can be incorporated by co-extrusion of a polymer substance within the drug-containing core, which will then form a third portion of the device, having a reinforcing member, a drug-containing core containing or surrounding the reinforcing member, and the porogen-containing shell. The reinforcing member can comprise a polymer with good mechanical strength and resilience, such as pure ethylene-vinyl acetate. The reinforcing member can be a metal wire made of a biocompatible metal, such as gold, copper, aluminum, or stainless steel.

Producing rod-shaped devices by co-extrusion, followed by cutting the extruded rod, results in a cylinder-shaped rod. The two ends of the cylinder (the bases of the cylinder) will have an exposed core region. In order to prevent elution of drug from the exposed core region at either end of the device, one or both ends of the device can be capped with a capping material. The capping material can be a polymer, such as ethylene-vinyl acetate, silicone, or an erodible polymer. The capping material can be 1 mm thick, 2 mm thick, or 3 mm thick. The capping material can be impermeable to the core pharmaceutical substance, which serves to prevent elution of core pharmaceutical substance from the ends of the device. The capping material can be permeable to the core pharmaceutical substance, which serves to regulate elution of core pharmaceutical substance from the ends of the device.

Chemical Composition of Devices of the Invention

CORE: the core of the device comprises polymer and drug. In one embodiment, the core comprises about 40% to about 80% drug, such as $T_3$, or about 45% to about 75% drug, such as $T_3$, or about 50% to about 70% drug, such as $T_3$, or about 55% to about 65% drug, such as $T_3$, or about 60% drug, such as $T_3$. The balance of the core is made up of polymer; a preferred polymer is ethylene-vinyl acetate (EVA). EVA blends can have about 60% to about 75% ethylene content and about 40% to about 25% vinyl acetate content. A preferred EVA blend has about 33% vinyl acetate content.

SHELL: the shell of the device comprises polymer and a porogen. A preferred porogen is ethylcellulose. In one embodiment, the shell contains about 1% to about 80% porogen, such as ethylcellulose, or about 1% to about 40% porogen, such as ethylcellulose, or about 30% to about 80% porogen, such as ethylcellulose, or about 5% to about 25% porogen, such as ethylcellulose, or about 5% to about 15% porogen, such as ethylcellulose, or about 25% to about 50% porogen, such as ethylcellulose, or about 30% to about 60% porogen, such as ethylcellulose, or about 35% to about 55% porogen, such as ethylcellulose, or about 40% to about 50% porogen, such as ethylcellulose, or about 30% to about 40% porogen, such as ethylcellulose, or about 50% to about 60% porogen, such as ethylcellulose. The balance of the shell is made up of polymer. In one embodiment, the same polymer is used for the shell as is used for the core, such as EVA, such as EVA with about 33% vinyl acetate. In another embodiment, a different polymer is used for the shell than the polymer used for the core.

Additional preferred porogens are citric acid and benzoic acid, or salts of citric acid or benzoic acid, such as sodium and potassium salts. Citric acid and benzoic acid are particularly useful as shell porogens in an implant with an EVA shell, or an implant with an EVA shell and an EVA core. Citric acid and benzoic acid are inexpensive, commonly available in USP/NF grades, and can be readily identified by their ultraviolet absorbance signatures during routine HPLC analysis. Benzoic acid has particularly strong characteristic absorptions at 227 (=$\lambda_{max}$) and 275 nm. In one embodiment, the shell contains about 1% to about 80% porogen, such as benzoic acid, a benzoic acid salt, citric acid, or a citric acid salt, or about 1% to about 40% porogen, such as benzoic acid, a benzoic acid salt, citric acid, or a citric acid salt, or about 30% to about 80% porogen, such as benzoic acid, a benzoic acid salt, citric acid, or a citric acid salt, or about 5% to about 25% porogen, such as benzoic acid, a benzoic acid salt, citric acid, or a citric acid salt, or about 5% to about 15% porogen, such as benzoic acid, a benzoic acid salt, citric acid, or a citric acid salt, or about 25% to about 50% porogen, such as benzoic acid, a benzoic acid salt, citric acid, or a citric acid salt, or about 30% to about 60% porogen, such as benzoic acid, a benzoic acid salt, citric acid, or a citric acid salt, or about 35% to about 55% porogen, such as benzoic acid, a benzoic acid salt, citric acid, or a citric acid salt, or about 40% to about 50% porogen, such as benzoic acid, a benzoic acid salt, citric acid, or a citric acid salt, or about 30% to about 40% porogen, such as benzoic acid, a benzoic acid salt, citric acid, or a citric acid salt, or about 50% to about 60% porogen, such as benzoic acid, a benzoic acid salt, citric acid, or a citric acid salt, or about 60% to about 70% porogen, such as benzoic acid, a benzoic acid salt, citric acid, or a citric acid salt, or about 50% to about 70% porogen, such as benzoic acid, a benzoic acid salt, citric acid, or a citric acid salt, or about 50% to about 80% porogen, such as benzoic acid, a benzoic acid salt, citric acid, or a citric acid salt. The balance of the shell is made up of polymer. In one embodiment, the same polymer is used for the shell as is used for the core, such as EVA, such as EVA with about 33% vinyl acetate. In another embodiment, a different polymer is used for the shell than the polymer used for the core.

Benzoic acid is alcohol-soluble, and can be readily removed from the porogenic shells. Benzoic acid is also currently approved by the United States Food and Drug Administration for topical, oral, rectal, vaginal, intramuscular, and intravenous routes of administration. Relative to citric acid, benzoic acid is less corrosive toward metal processing equipment. In addition, benzoic acid has a melting point of 120° C., and can serve as a surface glidant for the compounded polymer-porogen extrudate as it passes through a heated nozzle.

In some embodiments of the invention, the devices additionally comprise a radiopaque substance. The radiopaque substance is preferably opaque to X-ray radiation. The radiopaque substance aids in precisely locating the implant in a non-invasive manner, for example, in an X-ray or CT scan. The radiopaque substance can be located in the core, in the shell, or in both the core and the shell. Barium sulfate is a preferred radiopaque substance. Other radiopaque substances which can be used include, but are not limited to, zirconium oxide, bismuth oxide, bismuth salts, and calcium tungstate.

In some embodiments of the invention, the devices additionally comprise a substance which is detectable by magnetic resonance imaging, for use in locating the implant during an MRI scan. The substance detectable by magnetic resonance imaging can be located in the core, in the shell, or in both the core and the shell.

In some embodiments of the invention, the devices additionally comprise both a radiopaque substance and a substance which is detectable by magnetic resonance imaging. The substance detectable by magnetic resonance imaging can be located in the core, in the shell, or in both the core and the shell, and the radiopaque substance can be located in the core, in the shell, or in both the core and the shell.

Reduction of Burst Release Using Devices of the Invention

Burst release from the devices of the invention is reduced compared to previously used devices; see FIG. 12A, FIG. 12B, FIG. 13A, and FIG. 13B for examples of reduction of burst release. The devices of the invention can be prepared with varying percentages of porogen and varying sizes of porogen to adjust the reduction of burst release as compared to devices without porogen. In some embodiments, burst release is reduced by at least about three orders of magnitude. In some embodiments, burst release is reduced by up to about three orders of magnitude. In some embodiments, burst release is reduced by about two to about three orders of magnitude. In some embodiments, burst release is reduced by at least about two orders of magnitude. In some embodiments, burst release is reduced by up to about two orders of magnitude. In some embodiments, burst release is reduced by about two orders of magnitude. In some embodiments, burst release is reduced by about one to about two orders of magnitude. In some embodiments, burst release is reduced by at least about one order of magnitude. In some embodiments, burst release is reduced by up to about one order of magnitude. In some embodiments, burst release is reduced by about one order of magnitude. In some embodiments, burst release is reduced by about 50%.

The initial period over which burst release is measured for comparison can be the first hour after implantation, the first six hours after implantation, the first 12 hours after implantation, the first 24 hours after implantation, the first 48 hours after implantation, the first three days after implantation, the first four days after implantation, the first five days after implantation, the first six days after implantation, the first seven days after implantation, the first eight days after implantation, the first nine days after implantation, or the first ten days after implantation.

Pharmaceutical Substance and Drugs for Use in Devices

A variety of pharmaceutical substances and drugs can be used in the devices of the invention. In one embodiment, the pharmaceutical substance or drug in the core comprises a substance selected from the group consisting of L-thyroxine ($T_4$), L-triiodothyronine ($T_3$), or a combination thereof. In one embodiment, the pharmaceutical substance or drug in the core comprises L-triiodothyronine ($T_3$). In one embodiment, the pharmaceutical substance or drug in the core comprises L-thyroxine ($T_4$). In one embodiment, the pharmaceutical substance or drug in the core comprises a combination of L-thyroxine ($T_4$) and L-triiodothyronine ($T_3$).

In one embodiment, the pharmaceutical substance or drug in the core can comprise ropinirole. In one embodiment, the pharmaceutical substance or drug in the core can comprise tenofovir. In one embodiment, the pharmaceutical substance or drug in the core can comprise emtricitabine. In one embodiment, the pharmaceutical substance or drug in the core can comprise a combination of tenofovir and emtricitabine. In one embodiment, the pharmaceutical substance or drug in the core can comprise bosentan. In one embodiment, the pharmaceutical substance or drug in the core can comprise methylphenidate. In one embodiment, the pharmaceutical substance or drug in the core can comprise liraglutide. In one embodiment, the pharmaceutical substance or drug in the core can comprise atovaquone, proguanil, or a combination of atovaquone and proguanil. In one embodiment, the pharmaceutical substance or drug in the core can comprise nalmefene.

In one embodiment, the pharmaceutical substance or drug in the core can comprise doxycycline, atovaquone, proguanil, or a combination of atovaquone and proguanil.

Any of the pharmaceutical substances or drugs that can be used in the core can also be used as shell pharmaceutical substances in implants and methods that have a shell pharmaceutical substance.

Any of the pharmaceutical substances or drugs described herein can be used in their non-salt form, or as a salt of the pharmaceutical substance or drug. Any of the pharmaceutical substances or drugs described herein can be used in their non-solvate or non-hydrate form, or as a solvate or hydrate of the pharmaceutical substance or drug.

Diseases Treatable with Devices of the Invention

The devices of the invention can be used in methods of treatment of various diseases. Such diseases include hypothyroidism, metabolic syndrome, hyperlipidemia, and obesity (using devices comprising $T_3$, $T_4$, or a combination of $T_3$ and $T_4$), Parkinson's disease (using devices comprising ropinirole), restless leg syndrome (RLS) (using devices comprising ropinirole), pre-exposure prophylaxis of HIV or other retroviral acquisition or the treatment of HIV and other retroviral infection (using devices comprising tenofovir, emtricitabine, or a combination of tenofovir and emtricitabine); pulmonary arterial hypertension (using devices comprising bosentan), attention deficit/hyperactivity disorder (using devices comprising methylphenidate), and type 2 diabetes (using devices comprising liraglutide). The devices of the invention can also be used for treating obesity and for weight loss (using devices comprising liraglutide). The devices of the invention can also be used for treating malaria, or for prophylaxis against malaria (using devices comprising doxycycline, atovaquone, proguanil, or a combination of atovaquone and proguanil). The devices of the invention can also be used for treating alcoholism or alcohol addiction (using devices comprising nalmefene).

Exemplary Polymers for Use in Devices

As noted above, a preferred polymer for use in both the core and shell of the implants is ethylene vinyl acetate (EVA). However, other polymers can be used in the invention. As used herein, a "polymer" or "polymeric material" means a macromolecule comprising repeating monomer units or co-monomer units. The polymer may be bioerodible or non-bioerodible. The polymer may be a homopolymer, copolymer, terpolymer, or may contain more than three monomers. The polymer is preferably biocompatible.

Exemplary polymers that can be used for making devices of the invention include: acrylics, agarose, alginate, and combinations, cellulose ethers, collagen, copolymers containing poly(ethylene glycol) and poly butylene terephthalate segments (PEG/PBT) (Poly Active™), copolymers of poly(lactic) and glycolic acid, copolymers thereof with poly(ethylene glycol), derivatives and mixtures thereof, dextran, dextrose, elastin, epoxides, ethylene vinyl acetate (EVA copolymer), fluoropolymers, gelatin, hydroxypropylmethylcellulose, maleic anhydride copolymers, methyl cellulose and ethyl cellulose, non-water soluble cellulose acetate, non-water soluble chitosan, non-water soluble hydroxyethyl cellulose, non-water soluble hydroxypropyl cellulose, peptides, PLLA-polyglycolic acid (PGA) copolymer (also known as poly-L-lactic acid-co-glycolic acid, or PLGA), poly (L-lactic acid), poly(2-ethoxyethyl methacrylate), poly (2-hydroxyethyl methacrylate), poly(2-methoxyethyl acrylate), poly(2-methoxyethyl methacrylate), poly(acrylamide), poly(alginic acid), poly(amino acids), poly(anhydrides), poly(aspartic acid), poly(benzyl glutamate), poly(beta-hydroxy butyrate), poly(caprolactone), poly(D,L-lactic acid), poly(D,L-lactide) (PLA), poly(D,L-lactide-co-caprolactone) (PLA/PCL) and poly(glycolide-co-caprolactone) (PGA/PCL), poly(D,L-lactide-co-glycolide) (PLA/PGA), poly (etherurethane urea), poly(ethyl glutamate-co-glutamic acid), poly(ethylene carbonate), poly(ethylene glycol), poly (ethylene-co-vinyl alcohol), poly(glutamic acid), poly(glutamic acid-co-ethyl glutamate), poly(glycolic acid), poly (glycolide-co-trimethylene carbonate) (PGA/PTMC), poly (hydroxypropyl methacrylamide), poly(imino carbonates), poly(leucine), poly(leucine-co-hydroxyethyl glutamine), poly(L-lactide-co-D,L-lactide) (PLLA/PLA), poly(L-lactide-co-glycolide) (PLLA/PGA), poly(lysine), poly(ortho esters), poly(orthoesters), poly(oxaamides), poly(oxaesters), poly(phosphate ester), poly(phosphazene), poly(phospho esters), poly(phosphoesters), poly(propylene carbonate), poly(propylene glycol), poly(pyrrole), poly(tert-butyloxycarbonylmethyl glutamate), poly(tetramethylene glycol), poly(trimethylene carbonate), poly(ureas), poly(urethanes), poly(urethane-ureas), poly(vinyl alcohol), poly(vinyl alcohol-co-vinyl acetate), high molecular weight poly(vinylpyrrolidone) (PVP), poly[(97.5% dimethyl-trimethylene carbonate)-co-(2.5% trimethylene carbonate)], polyacrylic acid, polyalkylene oxides, polyamides, polycaprolactone (PCL) poly-(hydroxy butyrate-co-hydroxyvalerate) copolymer (PHBV), polycaprolactone (PCL), polycaprolactone co-butylacrylate, polydepsipeptides, polydioxanone (PDS), polyesters, polyethylene glycol, polyethylene oxide (PEO), polyethylene terephthalate (PET), polyglycolic acid and copolymers and mixtures thereof such as poly(L-lactide) (PLLA), polyglycolic acid[polyglycolide (PGA)], polyhydroxy butyrate (PHBT) and copolymers of polyhydroxy butyrate, polyiminocarbonates, polylactic acid, polymethacrylic acid, polyolefins, polyphosphazene polymers, polypropylene fumarate, polysaccharides such as hyaluronic acid, polytetrafluoroethylene (PTFE Teflon®), polyurethanes, silicones, tyrosine-derived polyarylates, tyrosine-derived polycarbonates, tyrosine-derived polyiminocarbonates, tyrosine-derived polyphosphonates, urethanes, and combinations, derivatives and mixtures thereof.

Exemplary erodible or bioerodible polymers that can be used for making devices of the invention include erodible or bioerodible forms of polyamide, aliphatic polycarbonates, polyalkylcyanoacrylate, polyalkylene oxalates, polyanhydride, polycarboxylic acid, polyester, poly(hydroxy butyrate), polyimide, poly(iminocarbonate), polycaprolactone (PCL), poly-D,L-lactic acid (DL-PLA), polydioxanone, poly(glycolic acid), poly-L-lactic acid (L-PLA), poly-L-lactic acid-co-glycolic acid (PLGA), polyorthoester, polyphosphazenes, and polyphosphoester, poly(trimethylene carbonate), and derivatives and mixtures thereof. The polymer may also be formed from a material selected from the group consisting of cellulose ester, poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, and derivatives and combinations thereof.

Additional representative examples of the polymer for use in the invention include, but are not limited to, ABS resins, acrylic polymers and copolymers, acrylonitrile-styrene copolymers, alkyd resins, and carboxymethyl cellulose, and ethylene-vinyl acetate copolymers, cellophane, cellulose butyrate, cellulose acetate butyrate, cellulose acetate, cellulose ethers, cellulose nitrate, cellulose propionate, copolymers of vinyl monomers with each other and olefins, ethylene-methyl methacrylate copolymers, epoxy resins, ethylene vinyl alcohol copolymer (commonly known by the generic name EVOH or by the trade name EVAL), poly (glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, such as Nylon 66 and polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, such as polystyrene, polyvinyl esters, such as polyvinyl acetate, polyvinyl ethers, such as polyvinyl methyl ether, polyvinylidene halides, such as vinylidene fluoride based homo- or co-polymer under the trade name Solef™ or Kynar™, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, such as polyvinyl chloride, copolymers of these polymers with poly(ethylene glycol) (PEG), or combinations thereof.

In some embodiments, the polymer can be copolymers of poly(lactic) and glycolic acid, poly(anhydrides), poly(D,L-lactic acid), poly(D,L-lactide), poly(D,L-lactide-co-glycolide), poly(ethylene carbonate), poly(glycolic acid), poly (glycolide), poly(L-lactic acid), poly(L-lactide), poly(L-lactide-co-glycolide), poly(ortho esters), poly(oxaamides), poly(oxaesters), poly(phosphazenes), poly(phospho esters), poly(phosphoesters), poly(propylene carbonate), poly(trimethylene carbonate), poly(tyrosine derived carbonates), poly (tyrosine derived iminocarbonates), poly(tyrosine derived arylates), copolymers of these polymers with poly(ethylene glycol) (PEG), or combinations thereof.

Examples of non-bioerodible polymers useful in the present invention include poly(ethylene-co-vinyl acetate) (EVA), polyvinylalcohol and polyurethanes, such as polycarbonate-based polyurethanes.

As previously noted, a preferred polymer for both the core and the shell of the devices of the invention is ethyl vinyl acetate (EVA).

The devices can comprise a single type of polymer or a mixture of two or more polymers. A mixture of two polymers may modulate the release rate of the drug. It is desirable that an effective therapeutic amount of the drug be released from a device of the invention for a reasonably long period of time. U.S. Pat. No. 6,258,121 to Yang et al. disclosed a method of altering the release rate by blending two polymers with differing release rates and incorporating them into a single layer: this technique can also aid in reducing burst release of drug upon implant.

Exemplary Porogens

Examples of porogens which can be used in the shell can include alkyl celluloses and hydroxyalkyl celluloses, such as ethylcellulose, methylcellulose, and hydroxy methylcellulose; fatty acids such as stearic acid, palmitic acid, myristic acid, and linoleic acid; biocompatible salts, such as sodium chloride, calcium chloride, or sodium phosphate; and soluble polymers such as low molecular weight polyvinylpyrollidone (PVP). Porogen particles are preferably used in a tight size distribution to enable control over the size of the pores. The mean diameter of the porogens used can be between about 1 micrometer and about 300 micrometers. In some embodiments, the mean diameter of the porogens is greater than the thickness of the shell. In some embodiments, the mean diameter of the porogens is about equal to the thickness of the shell. In some embodiments, the mean diameter of the porogens is less than the thickness of the shell. In some embodiments, the mean diameter of the porogens is less than about 75% of the thickness of the shell. In some embodiments, the mean diameter of the porogens is less than about 50% of the thickness of the shell. In some embodiments, the mean diameter of the porogens is less than about 25% of the thickness of the shell.

The porogens (porogenic materials) function to create pores in the shell of the implantable device, and in preferred embodiments, are not pharmaceutically active substances or drugs. In alternate preferred embodiments, porogens (porogenic materials) are not pharmaceutically active substances or drugs for the disease or condition which the implantable device is intended to treat. Thus, for example, when the porogen is citric acid, the implantable device is not intended to treat a disease or condition for which citric acid is useful for treatment.

In some embodiments, the porogen material comprises spherical particles or approximately spherical particles, and at least about 90% of the particles have a diameter between about 1 micrometer and about 50 micrometers. In some embodiments, the porogen material comprises spherical particles or approximately spherical particles, with a mean diameter between about 1 micrometer and about 50 micrometers. In some embodiments, the porogen material comprises spherical particles or approximately spherical particles, and at least about 90% of the particles have a diameter that varies by about 10% or less from a mean diameter.

In some embodiments, the porogen material comprises particles and the longest dimension of at least about 90% of the particles is between about 1 micrometer and about 50 micrometers. In some embodiments, the porogen material comprises particles and the longest dimension of the particles is between about 1 micrometer and about 50 micrometers. In some embodiments, the porogen material comprises particles and the longest dimension of at least about 90% of the particles varies by 10% or less from the average longest dimension of the particles.

In some embodiments, the porogen material comprises particles and the mean dimension of at least about 90% of the particles is between about 1 micrometer and about 50 micrometers, where the mean dimension of the particles is the mean of the longest dimension of the particles and the shortest dimension of the particles. In some embodiments, the porogen material comprises particles and the mean dimension of the particles is between about 1 micrometer and about 50 micrometers. In some embodiments, the porogen material comprises particles and the mean dimension of at least about 90% of the particles varies by 10% or less from the average of the mean dimension of the particles.

The mean diameter of the porogen particles, such as spherical particles or approximately spherical particles, can be between about 1 micrometer and about 300 micrometers. In one embodiment, at least about 90% of the particles have a diameter that varies by about 10% or less from a mean diameter, where the mean diameter is between about 1 micrometer and about 300 micrometers. In one embodiment, at least about 90% of the particles have a diameter that varies by about 10% or less from a mean diameter, where the mean diameter is between about 1 micrometer and about 200 micrometers. In one embodiment, at least about 90% of the particles have a diameter that varies by about 10% or less from a mean diameter, where the mean diameter is between about 1 micrometer and about 100 micrometers. In one embodiment, at least about 90% of the particles have a diameter that varies by about 10% or less from a mean diameter, where the mean diameter is between about 1 micrometer and about 50 micrometers. In one embodiment, at least about 90% of the particles have a diameter that varies by about 10% or less from a mean diameter, where the mean diameter is between about 1 micrometer and about 30 micrometers. In one embodiment, at least about 90% of the particles have a diameter that varies by about 10% or less from a mean diameter, where the mean diameter is between about 1 micrometer and about 25 micrometers. In one embodiment, at least about 90% of the particles have a diameter that varies by about 10% or less from a mean diameter, where the mean diameter is between about 1 micrometer and about 20 micrometers. In one embodiment, at least about 90% of the particles have a diameter that varies by about 10% or less from a mean diameter, where the mean diameter is between about 1 micrometer and about 10 micrometers. In one embodiment, at least about 90% of the particles have a diameter that varies by about 10% or less from a mean diameter, where the mean diameter is between about 1 micrometer and about 5 micrometers.

In one embodiment, at least about 75% of the particles have a diameter less than about 300 micrometers. In one embodiment, at least about 75% of the particles have a diameter less than about 200 micrometers. In one embodiment, at least about 75% of the particles have a diameter less than about 100 micrometers. In one embodiment, at least about 75% of the particles have a diameter less than about 50 micrometers. In one embodiment, at least about 75% of the particles have a diameter less than about 30 micrometers. In one embodiment, at least about 75% of the particles have a diameter less than about 25 micrometers. In one embodiment, at least about 75% of the particles have a diameter less than about 20 micrometers. In one embodiment, at least about 75% of the particles have a diameter less than about 10 micrometers. In one embodiment, at least about 75% of the particles have a diameter less than about 5 micrometers.

In one embodiment, at least about 90% of the particles have a diameter less than about 300 micrometers. In one embodiment, at least about 90% of the particles have a diameter less than about 200 micrometers. In one embodiment, at least about 90% of the particles have a diameter less than about 100 micrometers. In one embodiment, at least about 90% of the particles have a diameter less than about 50 micrometers. In one embodiment, at least about 90% of the particles have a diameter less than about 30 micrometers. In one embodiment, at least about 90% of the particles have a diameter less than about 25 micrometers. In one embodiment, at least about 90% of the particles have a diameter less than about 20 micrometers. In one embodiment, at least about 90% of the particles have a diameter less than about 10 micrometers. In one embodiment, at least about 90% of the particles have a diameter less than about 5 micrometers.

For particles which are non-spherical or irregularly shaped, such as needle-type particles, the particles can be characterized by their longest dimension. The mean longest dimension of the porogens can be between about 1 micrometer and about 300 micrometers. In one embodiment, at least about 90% of the particles have a longest dimension that varies by about 10% or less from a mean longest dimension, where the mean longest dimension is between about 1 micrometer and about 300 micrometers. In one embodiment, at least about 90% of the particles have a longest dimension that varies by about 10% or less from a mean longest dimension, where the mean longest dimension is between about 1 micrometer and about 200 micrometers. In one embodiment, at least about 90% of the particles have a longest dimension that varies by about 10% or less from a mean longest dimension, where the mean longest dimension is between about 1 micrometer and about 100 micrometers. In one embodiment, at least about 90% of the particles have a longest dimension that varies by about 10% or less from a mean longest dimension, where the mean longest dimension is between about 1 micrometer and about 50 micrometers. In one embodiment, at least about 90% of the particles have a longest dimension that varies by about 10% or less from a mean longest dimension, where the mean longest dimension is between about 1 micrometer and about 30 micrometers. In one embodiment, at least about 90% of the particles have a longest dimension that varies by about 10% or less from a mean longest dimension, where the mean longest dimension is between about 1 micrometer and about 25 micrometers. In one embodiment, at least about 90% of the particles have a longest dimension that varies by about 10% or less from a mean longest dimension, where the mean longest dimension is between about 1 micrometer and about 20 micrometers. In one embodiment, at least about 90% of the particles have a longest dimension that varies by about 10% or less from a mean longest dimension, where the mean longest dimension is between about 1 micrometer and about 10 micrometers. In one embodiment, at least about 90% of the particles have a longest dimension that varies by about 10% or less from a mean longest dimension, where the mean longest dimension is between about 1 micrometer and about 5 micrometers.

In one embodiment, at least about 75% of the particles have a longest dimension less than about 300 micrometers. In one embodiment, at least about 75% of the particles have a longest dimension less than about 200 micrometers. In one embodiment, at least about 75% of the particles have a longest dimension less than about 100 micrometers. In one embodiment, at least about 75% of the particles have a longest dimension less than about 50 micrometers. In one embodiment, at least about 75% of the particles have a longest dimension less than about 30 micrometers. In one embodiment, at least about 75% of the particles have a longest dimension less than about 25 micrometers. In one embodiment, at least about 75% of the particles have a longest dimension less than about 20 micrometers. In one embodiment, at least about 75% of the particles have a longest dimension less than about 10 micrometers. In one embodiment, at least about 75% of the particles have a longest dimension less than about 5 micrometers.

In one embodiment, at least about 90% of the particles have a longest dimension less than about 300 micrometers. In one embodiment, at least about 90% of the particles have a longest dimension less than about 200 micrometers. In one embodiment, at least about 90% of the particles have a longest dimension less than about 100 micrometers. In one embodiment, at least about 90% of the particles have a longest dimension less than about 50 micrometers. In one embodiment, at least about 90% of the particles have a longest dimension less than about 30 micrometers. In one embodiment, at least about 90% of the particles have a longest dimension less than about 25 micrometers. In one embodiment, at least about 90% of the particles have a longest dimension less than about 20 micrometers. In one embodiment, at least about 90% of the particles have a longest dimension less than about 10 micrometers. In one embodiment, at least about 90% of the particles have a longest dimension less than about 5 micrometers.

For particles which are non-spherical or irregularly shaped, such as needle-type particles, the particles can be also characterized by the mean of their longest dimension and shortest dimension ("mean of LD and SD"). The average mean of LD and SD of the porogens can be between about 1 micrometer and about 300 micrometers. In one embodiment, at least about 90% of the particles have a mean of LD and SD that varies by about 10% or less from an average mean of LD and SD, where the average mean of LD and SD is between about 1 micrometer and about 300 micrometers. In one embodiment, at least about 90% of the particles have a mean of LD and SD that varies by about 10% or less from an average mean of LD and SD, where the average mean of LD and SD is between about 1 micrometer and about 200 micrometers. In one embodiment, at least about 90% of the particles have a mean of LD and SD that varies by about 10% or less from an average mean of LD and SD, where the average mean of LD and SD is between about 1 micrometer and about 100 micrometers. In one embodiment, at least about 90% of the particles have a mean of LD and SD that varies by about 10% or less from an average mean of LD and SD, where the average mean of LD and SD is between about 1 micrometer and about 50 micrometers. In one embodiment, at least about 90% of the particles have a mean of LD and SD that varies by about 10% or less from an average mean of LD and SD, where the average mean of LD and SD is between about 1 micrometer and about 30 micrometers. In one embodiment, at least about 90% of the particles have a mean of LD and SD that varies by about 10% or less from an average mean of LD and SD, where the average mean of LD and SD is between about 1 micrometer and about 25 micrometers. In one embodiment, at least about 90% of the particles have a mean of LD and SD that varies by about 10% or less from an average mean of LD and SD, where the average mean of LD and SD is between about 1 micrometer and about 20 micrometers. In one embodiment, at least about 90% of the particles have a mean of LD and SD that varies by about 10% or less from an average mean of LD and SD, where the average mean of LD and SD is between about 1 micrometer and about 10 micrometers. In one embodiment, at least about 90% of the particles have a mean of LD and SD that varies by about 10% or less from an average mean of LD and SD, where the average mean of LD and SD is between about 1 micrometer and about 5 micrometers.

In one embodiment, at least about 75% of the particles have a mean of LD and SD less than about 300 micrometers. In one embodiment, at least about 75% of the particles have a mean of LD and SD less than about 200 micrometers. In one embodiment, at least about 75% of the particles have a mean of LD and SD less than about 100 micrometers. In one embodiment, at least about 75% of the particles have a mean of LD and SD less than about 50 micrometers. In one embodiment, at least about 75% of the particles have a mean of LD and SD less than about 30 micrometers. In one embodiment, at least about 75% of the particles have a mean of LD and SD less than about 25 micrometers. In one embodiment, at least about 75% of the particles have a mean of LD and SD less than about 20 micrometers. In one embodiment, at least about 75% of the particles have a mean of LD and SD less than about 10 micrometers. In one embodiment, at least about 75% of the particles have a mean of LD and SD less than about 5 micrometers.

In one embodiment, at least about 90% of the particles have a mean of LD and SD less than about 300 micrometers. In one embodiment, at least about 90% of the particles have a mean of LD and SD less than about 200 micrometers. In one embodiment, at least about 90% of the particles have a mean of LD and SD less than about 100 micrometers. In one embodiment, at least about 90% of the particles have a mean of LD and SD less than about 50 micrometers. In one embodiment, at least about 90% of the particles have a mean of LD and SD less than about 30 micrometers. In one embodiment, at least about 90% of the particles have a mean of LD and SD less than about 25 micrometers. In one embodiment, at least about 90% of the particles have a mean of LD and SD less than about 20 micrometers. In one embodiment, at least about 90% of the particles have a mean of LD and SD less than about 10 micrometers. In one embodiment, at least about 90% of the particles have a mean of LD and SD less than about 5 micrometers.

A single material can be used as the porogen used in the shell. Alternatively, two or more different porogen materials can be used.

Manufacture of Devices of the Invention

In some embodiments, the implantable devices of the invention can be produced by co-extruding the drug-containing core of the device and the porogen-containing shell. The drug substance is reduced to fine particles by milling (e.g., ball-milling, impact-milling), spray-drying, solvent precipitation, screening, or other method or combination of methods known in the art to produce fine particles. The drug can be combined with a polymer which is also prepared as fine particles to form the mixture used to make the drug-containing core. Likewise, the porogen-containing shell is prepared by blending fine particles of polymer with particles of porogen of the desired size. Each blended mixture is heated to a temperature suitable for extrusion, such as the softening point of the polymer. At this point, optionally and if necessary, either or both of the softened mixtures can be homogenized. The mixtures are then co-extruded, e.g., via Microtruder screw extruder, Model No. RCP-025, Randcastle Extrusion Systems, Cedar Grove, NJ, or via other extrusion devices known in the industry. The diameter of extrusion, as well as temperature, pressure and other parameters can be controlled as appropriate for each drug and polymer.

The extrudate can be extruded horizontally and collected for further processing. The extrudate can be cut into desirable lengths, e.g., from about 1 to about 3 cm. The extrudate can then be washed in a solvent, such as a solvent which dissolves and removes excess drug from the surface of the implant, or a solvent which assists in sterilization. Washing with or immersing in solvents which remove the porogen from the shell can also be used if it is desired that the porogen be removed prior to implantation. Examples of solvents which can be used for washing the implant include water, saline, aqueous buffers, and alcohols such as ethanol or isopropanol. Mixtures of water and alcohols can also be used, such as ethanol-water mixtures. Preferable solvents are 100% ethanol or water-ethanol mixtures. The implants can then be dried and packaged.

Washing may be followed by drying to remove the solvent. Drying is typically done between about 30° C. and about 60° C. for about 6 to about 24 hours, such as at about 40° C. for about 12 hours.

Drying may be followed by packaging and sterilization. Implants may be vacuum-packed in moisture barrier foil pouches, heat-sealed and/or vacuum-sealed, and then sterilized using gamma irradiation, such as about 20 to 30 kilograys, or about 25 kilograys, or about 2.5 to about 3.5 Megarad, or about 2.9 to about 3.1 Mrads, or about 3 Mrads.

Pharmacological Properties of Devices

Pharmacokinetics

The implants can provide an approximately constant blood level. The level of drug delivery is preferably within the therapeutic range of the drug, and lower than a level that might cause toxicity. In one embodiment, devices of the invention can comprise multiple drugs. In one embodiment, more than one implantable device may be inserted into a patient to achieve a desired level of drug concentration in the blood.

Total serum $T_3$ (i.e., both free $T_3$ and protein-bound $T_3$) in a normal adult human ranges from about 0.9 to about 2.7 nmol/L (about 60 to about 180 ng/dL) (Klee G. G., Clinical Chemistry 42(1):155 (1996)). Accordingly, $T_3$-containing implants of the invention can be administered to a patient provide total $T_3$ levels of about 0.9 to about 2.7 nmol/L (about 60 to about 180 ng/dL), or about 1.2 to about 2.7 nmol/L (about 80 to about 180 ng/dL). $T_3$-containing implants of the invention can be administered to a patient to result in a thyroid-stimulating hormone blood level of about 0.34 to about 4.82 uIU/mL.

Devices of the invention may be designed to provide a steady-state concentration of drug in the blood (e.g., in plasma or serum). Devices of the invention may be designed such that the resulting concentration of drug in the blood remains essentially constant over extended periods of time. Devices of the invention may be designed such that the resulting concentration of drug in the blood remains approximately constant over extended periods of time.

The release of drug from the devices of the invention is dependent on the rate of dissolution and on passive diffusion through the polymer matrix, and on other parameters.

Drug release rates are also affected by washing of the implant prior to insertion into the patient. The implants may be washed with a solvent such as water, ethanol, isopropanol, etc.

An "approximately constant blood level" refers to an approximately constant level of drug over a period of time in the blood of the subject or patient. As previously defined. "blood level" refers to the concentration of a drug, hormone, metabolite, or other substance in the blood of a subject, and can be measured in whole blood, blood serum, or blood plasma, as per standard clinical laboratory practice for the substance to be assayed. In one embodiment, an approximately constant blood level of drug varies by no more than about ±30% over a day, over a week, over a month, over three months, over six months, or over nine months, as compared to the mean or average blood level over that time period. In another embodiment, an approximately constant level of drug varies by no more than about ±20% over a day, over a week, over a month, over three months, over six months, or over nine months, as compared to the mean or average blood level over that time period. In another embodiment, an approximately constant level of drug varies by no more than about ±10% over a day, over a week, over a month, over three months, over six months, or over nine months, as compared to the mean or average blood level over that time period. An "approximately constant release rate" indicates that an approximately constant amount of the pharmaceutical substance is released from a device of the invention over a period of time, such as over a day, over a week, over a month, over three months, over six months, or over nine months. In some embodiments, the approximately constant release rate varies by no more than about ±50%, about ±40%, about ±30%, about ±20%, or about ±10% over the time period indicated, as compared to the average or mean release. An approximately constant release rate is preferred in order to achieve an approximately constant blood level. By "essentially constant" is meant that for about 95% of the extended period of time, the concentration of drug in blood is within about three, about two, or preferably about one standard deviation of the mean blood level. Measurements of the blood level can be performed hourly, twice a day, daily, twice a week, weekly, every two weeks, monthly, or at any other periodic interval for determination of the mean blood levels. For example, if the mean blood level of a drug sampled at weekly intervals is 2.0 ng/ml, and one standard deviation of the measurement is ±0.1 ng/ml, then blood levels that fall within about ±0.3 ng/ml, about ±0.2 ng/ml, or preferably about ±0.1 ng/ml for about 95% of the measurements are considered essentially constant. By "extended periods of time" is meant from a period of about 3 months to a period of about 1 year, or longer, e.g., an extended period of time can be about 3 months or at least about 3 months, about 4 months or at least about 4 months, about 5 months or at least about 5 months, about 6 months or at least about 6 months, about 9 months or at least about 9 months, about 12 months or at least about 12 months, about 15 months or at least about 15 months, about 18 months or at least about 18 months, about 21 months or at least about 21 months, about 24 months or at least about 24 months, or more than about 24 months.

Insertion and Removal of Drug Delivery Device

Another aspect of this invention is a method for delivering a pharmaceutical substance or drug to a patient in need thereof, comprising the step of inserting a device or devices as disclosed herein into the patient, wherein the pharmaceutical substance or drug is released from the device or devices into the patient. In a preferred method of this invention, devices of the invention are administered by subdermal implantation. In various embodiments, the devices are subdermally implanted at a site selected from a group consisting of the upper arm, scapular region, the back, the leg and the abdomen. Before implantation, the patient may be lightly anesthetized, e.g., with isoflurane or other anesthetic known in the art, and/or may have topical, transdermal, or subdermal anesthetic applied at the site of implantation. A small incision can be made through the skin and a trocar inserted subdermally, then loaded with one implant. The stylet can be inserted to hold the implant in place and the trocar carefully removed, leaving the implant in the subdermal space. Each site can be sutured closed and examined later. Complications such as skin irritation, inflammation, infection or other site-specific adverse effects can be monitored and treated, e.g., with antibiotics, as needed.

In various embodiments, devices of the invention can be left in the body for up to one year or more. The period of sustained release of drug into the body is thus from about 1 month to about 1 year, or longer, or from about 3 months to about 1 year or longer, e.g., at least about 3 months, at least about 6 months, at least about 9 months, at least about 12 months, at least about 15 months, at least about 18 months, at least about 21 months, or at least about 24 months or more. In some embodiments the devices can be left in the body for more than 1 year. Implants may be removed from the body at the end of the treatment period, through an incision, e.g., a 3-mm incision, using forceps.

A second implant may, for example, be used to deliver a pharmaceutical substance to counteract any adverse effects caused by a drug released from a first implant.

Multiple implants may be inserted into a single patient to regulate the delivery of a single drug, or to deliver several drugs.

EXEMPLARY EMBODIMENTS

The invention is further described by the following embodiments. The features of each of the embodiments are combinable with any of the other embodiments where appropriate and practical.

Embodiment 1. An implantable device for delivery of a pharmaceutical substance comprising a core comprising a first polymeric material and a core pharmaceutical substance; and a shell comprising a second polymeric material and a porogen material; wherein the implantable device has reduced burst release as compared to a comparison device made entirely of the first polymeric material and the core pharmaceutical substance.

Embodiment 2. The implantable device of embodiment 1, wherein the shell is a non-medicated layer.

Embodiment 3. The implantable device of embodiment 1, wherein the shell further comprises a shell pharmaceutical substance.

Embodiment 4. The implantable device of any one of embodiments 1-3, wherein the shell comprises about 1 wt % to about 80 wt % porogen material.

Embodiment 5. The implantable device of any one of embodiments 1-4, wherein the porogen material comprises spherical particles and at least about 90% of the spherical particles have a diameter between about 1 micrometer and about 50 micrometers.

Embodiment 6. The implantable device of any one of embodiments 1-5, wherein the porogen material comprises spherical particles with a mean diameter between about 1 micrometer and about 50 micrometers.

Embodiment 7. The implantable device of any one of embodiments 1-6, wherein the porogen material comprises spherical particles and at least about 90% of the spherical particles have a diameter that varies by 10% or less from a mean diameter.

Embodiment 8. The implantable device of any one of embodiments 1-7, wherein the porogen material comprises a bioerodible material.

Embodiment 9. The implantable device of any one of embodiments 1-7, wherein the porogen material comprises a non-bioerodible material.

Embodiment 10. The implantable device of any one of embodiments 1-7, wherein the porogen material comprises a material selected from the group consisting of an alkyl cellulose, a hydroxyalkyl cellulose, ethylcellulose, methylcellulose, hydroxymethylcellulose, a fatty acid, stearic acid, palmitic acid, myristic acid, linoleic acid, a biocompatible salt, sodium chloride, calcium chloride, and sodium phosphate.

Embodiment 11. The implantable device of any one of embodiments 1-7, wherein the porogen material comprises ethyl cellulose.

Embodiment 12. The implantable device of any one of embodiments 1-11, wherein the porogen material dissolves or dissociates from the shell upon washing the implantable device.

Embodiment 13. The implantable device of any one of embodiments 1-12, wherein the first polymeric material or the second polymeric material comprises a bioerodible material.

Embodiment 14. The implantable device of any one of embodiments 1-12, wherein the first polymeric material or the second polymeric material comprises a non-bioerodible material.

Embodiment 15. The implantable device of any one of embodiments 1-12, wherein the first polymeric material comprises one or more materials selected from the group consisting of polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

Embodiment 16. The implantable device of embodiment 15, wherein the first polymeric material comprises ethylene-vinyl acetate.

Embodiment 17. The implantable device of any one of embodiments 1-12, 15, and 16, wherein the second polymeric material comprises one or more materials selected from the group consisting of polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

Embodiment 18. The implantable device of embodiment 17, wherein the second polymeric material comprises ethylene-vinyl acetate.

Embodiment 19. The implantable device of any one of embodiments 1-18, wherein the implantable device is rod-shaped.

Embodiment 20. The implantable device of embodiment 19, wherein the implantable device has a diameter of about 1 mm to about 8 mm.

Embodiment 21. The implantable device of embodiment 19 or 20, wherein the implantable device has a length of about 10 mm to about 80 mm.

Embodiment 22. The implantable device of any one of embodiments 19-21, wherein the implantable device is capped at one end of the implantable device.

Embodiment 23. The implantable device of any one of embodiments 19-22, wherein the implantable device is capped at both ends of the implantable device.

Embodiment 24. The implantable device of any one of embodiments 1-23, wherein the core pharmaceutical substance comprises one or more substances selected from the group consisting of L-thyroxine (T4), L-triiodothyronine (T3), a combination of L-thyroxine (T4) and L-triiodothyronine (T3), ropinirole, tenofovir, emtricitabine, a combination of tenofovir and emtricitabine, bosentan, methylphenidate, and liraglutide.

Embodiment 25. The implantable device of any one of embodiments 1-24, wherein the core pharmaceutical substance comprises ropinirole or triiodothyronine.

Embodiment 26. The implantable device of any one of embodiments 1-25, wherein the core pharmaceutical substance comprises about 1 wt % to about 80 wt % of the core.

Embodiment 27. The implantable device of any one of embodiments 3-26, wherein the shell pharmaceutical substance comprises one or more substances selected from the group consisting of L-thyroxine (T4), L-triiodothyronine (T3), a combination of L-thyroxine (T4) and L-triiodothyronine (T3), ropinirole, tenofovir, emtricitabine, a combination of tenofovir and emtricitabine, bosentan, methylphenidate, and liraglutide.

Embodiment 28. The implantable device of any one of embodiments 3-27, wherein the shell pharmaceutical substance comprises ropinirole or triiodothyronine.

Embodiment 29. The implantable device of any one of embodiments 3-28, wherein the shell pharmaceutical substance comprises about 1 wt % to about 40 wt % of the outer layer.

Embodiment 30. The implantable device of any one of embodiments 3-29, further comprising a reinforcing member inside the core.

Embodiment 31. A method of forming an implantable device comprising extruding a first composition to form a core, the first composition comprising a first polymeric material and a core pharmaceutical substance; and coating the core with second composition to form a shell, the second composition comprising a second polymeric material and a porogen material.

Embodiment 32. A method of forming an implantable device comprising co-extruding a first composition and a second composition, where the first composition is extruded to form a core, the first composition comprising a first polymeric material and a core pharmaceutical substance; and the co-extruded second composition forming a shell around the core, the second composition comprising a second polymeric material and a porogen material.

Embodiment 33. The method of embodiment 31 or embodiment 32, wherein the first composition is formed by combining the first polymeric material with the core pharmaceutical substance.

Embodiment 34. The method of any one of embodiments 31-33, wherein the second composition is formed by combining the second polymeric material with the porogen material.

Embodiment 35. The method of any one of embodiments 31-34, further comprising washing the implantable device.

Embodiment 36. The method of embodiment 35, wherein the implantable device is washed in ethanol, water, or a mixture of ethanol and water.

Embodiment 37. The method of embodiment 35 or embodiment 36, wherein washing the device dissolves the porogen material or dissociates the porogen material from the implantable device to form a plurality of pores in the shell.

Embodiment 38. The method of any one of embodiments 31-37, wherein the second composition is a non-medicated material.

Embodiment 39. The method of any one of embodiments 31-38, wherein the second composition further comprises a shell pharmaceutical substance.

Embodiment 40. The method of any one of embodiments 31-39, wherein the second composition comprises about 1 wt % to about 80 wt % porogen materials.

Embodiment 41. The method of any one of embodiments 31-40, wherein the porogen materials comprise spherical particles and at least about 90% of the spherical particles have a diameter between about 1 micrometer and about 50 micrometers.

Embodiment 42. The method of any one of embodiments 31-41, wherein the porogen materials comprise spherical particles with a mean diameter between about 1 micrometer and about 50 micrometers.

Embodiment 43. The method of any one of embodiments 31-42, wherein the porogen materials comprise spherical particles and at least about 90% of the spherical particles have a diameter that varies by 10% or less from a mean diameter.

Embodiment 44. The method of any one of embodiments 31-43, wherein the porogen materials comprise a bioerodible material.

Embodiment 45. The method of any one of embodiments 31-43, wherein the porogen materials comprise a non-bioerodible material.

Embodiment 46. The method of any one of embodiments 31-43, wherein the porogen comprises a material selected from the group consisting of an alkyl cellulose, a hydroxyalkyl cellulose, ethylcellulose, methylcellulose, hydroxymethylcellulose, a fatty acid, stearic acid, palmitic acid, myristic acid, linoleic acid, a biocompatible salt, sodium chloride, calcium chloride, and sodium phosphate.

Embodiment 47. The method of embodiment 46, wherein the porogen materials comprise ethyl cellulose.

Embodiment 48. The method of any one of embodiments 31-47, wherein the first polymeric material or the second polymeric material comprises a bioerodible material.

Embodiment 49. The method of any one of embodiments 31-47, wherein the first polymeric material or the second polymeric material comprises a non-bioerodible material.

Embodiment 50. The method of any one of embodiments 31-47, wherein the first polymeric material comprises one or more materials selected from the group consisting of poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly (trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

Embodiment 51. The method of embodiment 50, wherein the first polymeric material comprises ethylene-vinyl acetate.

Embodiment 52. The method of any one of embodiments 31-47, 50, or 51, wherein the second polymeric material comprises one or more materials selected from the group consisting of poly butylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, ABS resins, acrylic polymers and copolymers, acrylonitrile-styrene copolymers, alkyd resins, ethylene-vinyl acetate copolymers, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxy butyrate-co-valerate), poly(hydroxyvalerate), poly(lactide-co-glycolide), poly(propylene fumarate), poly(trimethylene carbonate), polyacrylonitrile, polyamides, Nylon 66, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene halides, vinylidene fluoride based homo- or copolymer, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, polyvinyl chloride, and copolymers of these polymers with poly(ethylene glycol) (PEG).

Embodiment 53. The method of embodiment 52, wherein the second polymeric material comprises ethylene-vinyl acetate.

Embodiment 54. The method of any one of embodiments 31-53, wherein the implantable device is rod-shaped.

Embodiment 55. The method of any one of embodiments 31-54, wherein the implantable device has a diameter of about 1 mm to about 8 mm.

Embodiment 56. The method of any one of embodiments 31-55, wherein the implantable device has a length of about 10 mm to about 80 mm.

Embodiment 57. The method of any one of embodiments 31-56, further comprising capping the implantable device at one end of the implantable device.

Embodiment 58. The method of any one of embodiments 31-57, further comprising capping the implantable device at both ends of the implantable device.

Embodiment 59. The method of any one of embodiments 31-58, wherein the core pharmaceutical substance comprises one or more substances selected from the group consisting of L-thyroxine (T4), L-triiodothyronine (T3), a combination of L-thyroxine (T4) and L-triiodothyronine (T3), ropinirole, tenofovir, emtricitabine, a combination of tenofovir and emtricitabine, bosentan, methylphenidate, and liraglutide.

Embodiment 60. The method of any one of embodiments 31-59, wherein the core pharmaceutical substance comprises ropinirole or triiodothyronine.

Embodiment 61. The method of any one of embodiments 31-60, wherein the core pharmaceutical substance comprises about 1 wt % to about 80 wt % of the first composition.

Embodiment 62. The method of any one of embodiments 38-61, wherein the shell pharmaceutical substance comprises one or more substances selected from the group consisting of L-thyroxine (T4), L-triiodothyronine (T3), a combination of L-thyroxine (T4) and L-triiodothyronine (T3), ropinirole, tenofovir, emtricitabine, a combination of tenofovir and emtricitabine, bosentan, methylphenidate, and liraglutide.

Embodiment 63. The method of any one of embodiments 38-62, wherein the shell pharmaceutical substance comprises ropinirole or triiodothyronine.

Embodiment 64. The method of any one of embodiments 38-63, wherein the shell pharmaceutical substance comprises about 1 wt % to about 40 wt % of the second composition.

Embodiment 65. A method of treating a disease in a subject comprising implanting into the subject the implantable device according to any one of embodiments 1-30.

Embodiment 66. The method of embodiment 65, wherein the disease is hypothyroidism, Parkinson's disease, restless leg syndrome (RLS), HIV infection, retroviral infection, pulmonary arterial hypertension, attention deficit/hyperactivity disorder, type 2 diabetes, or obesity.

Embodiment 67. A method of providing pre-exposure prophylaxis of HIV or prophylaxis of retroviral acquisition, comprising implanting into the subject the implantable device according to any one of embodiments 1-30.

Embodiment 68. The method of any one of embodiments 65-67, wherein the implantable device releases an average of about 10 μg to about 150 μg of the core pharmaceutical substance per day for the first 30 days when implanted in the subject.

Embodiment 69. The method of any one of embodiments 64-68, wherein the implantable device releases the core pharmaceutical substance when implanted in the subject with a daily variance of less than about 10% from the daily average release for the first 30 days.

Embodiment 70. The method of any one of embodiments 64-68, wherein the implantable device releases the core pharmaceutical substance when implanted in the subject with an initial burst at least 50% lower than the initial burst from a comparison implant without the shell.

Embodiment 71. The method of any one of embodiments 64-68, wherein the implantable device releases the core pharmaceutical substance when implanted in the subject with an initial burst at least 50% lower than the initial burst from a comparison implant where the shell is replaced with additional core material.

Embodiment A1. An implantable device for delivery of a pharmaceutical substance comprising a core comprising a first polymeric material and a core pharmaceutical substance; and a shell comprising a second polymeric material and a porogen material.

Embodiment A2. The implantable device of embodiment A1, wherein the core diameter is between about 0.5 mm to about 3.5 mm, and the shell thickness is between about 0.25 mm to about 1.75 mm thickness.

Embodiment A3. The implantable device of embodiment A1, wherein the core diameter is between about 0.5 mm to about 3.5 mm, and the shell thickness is between about 0.25 mm to about 1.75 mm thickness, with the proviso that the sum of the core diameter plus twice the thickness of the shell does not exceed about 4 mm.

Embodiment A4. The implantable device of any one of embodiments A1-A3, wherein the core diameter is between about 1.5 mm to about 3 mm, and the shell thickness is between about 0.25 mm to about 0.75 mm.

Embodiment A5. The implantable device of any one of embodiments A1-A4, wherein the porogenic material comprises about 1% to about 80% of the shell.

Embodiment A6. The implantable device of any one of embodiments A1-A4, wherein the porogenic material comprises about 5% to about 25% of the shell.

Embodiment A7. The implantable device of any one of embodiments A1-A4, wherein the porogenic material comprises about 25% to about 50% of the shell.

Embodiment A8. The implantable device of any one of embodiments A1-A4, wherein the porogenic material comprises about 50% to about 70% of the shell.

Embodiment A9. The implantable device of any one of embodiments A1-A8, wherein the porogenic material is removed from the device prior to implantation.

Embodiment A10. The implantable device of any one of embodiments A1-A9, wherein the porogenic material comprises one or more of ethyl cellulose, benzoic acid, a benzoic acid salt, citric acid, or a citric acid salt.

Embodiment A11. The implantable device of any one of embodiments A1-A10, wherein the porogenic material comprises ethyl cellulose.

Embodiment A12. The implantable device of any one of embodiments A1-A10, wherein the porogenic material comprises benzoic acid.

Embodiment A13. The implantable device of any one of embodiments A1-A10, wherein the porogenic material comprises a benzoic acid salt.

Embodiment A14. The implantable device of any one of embodiments A1-A10, wherein the porogenic material comprises citric acid.

Embodiment A15. The implantable device of any one of embodiments A1-A10, wherein the porogenic material comprises a citric acid salt.

Embodiment A16. The implantable device of any one of embodiments A1-A15, wherein the porogenic material has a longest average dimension between about 5 micrometers and about 200 micrometers.

Embodiment A17. The implantable device of any one of embodiments A1-A15, wherein the porogenic material has a longest average dimension between about 10 micrometers and about 150 micrometers.

Embodiment A18. The implantable device of any one of embodiments A1-A15, wherein the porogenic material has a longest average dimension between about 5 micrometers and about 30 micrometers.

Embodiment A19. The implantable device of any one of embodiments A1-A18, wherein the core pharmaceutical substance is L-thyroxine (T4).

Embodiment A20. The implantable device of any one of embodiments A1-A18, wherein the core pharmaceutical substance is L-triiodothyronine (T3).

Embodiment A21. The implantable device of any one of embodiments A1-A18, wherein the core pharmaceutical substance is a combination of L-thyroxine (T4) and L-triiodothyronine (T3).

Embodiment A22. The implantable device of any one of embodiments A1-A18, wherein the core pharmaceutical substance is ropinirole.

Embodiment A23. The implantable device of any one of embodiments A1-A18, wherein the core pharmaceutical substance is tenofovir.

Embodiment A24. The implantable device of any one of embodiments A1-A18, wherein the core pharmaceutical substance is emtricitabine.

Embodiment A25. The implantable device of any one of embodiments A1-A18, wherein the core pharmaceutical substance is a combination of tenofovir and emtricitabine.

Embodiment A26. The implantable device of any one of embodiments A1-A18, wherein the core pharmaceutical substance is bosentan.

Embodiment A27. The implantable device of any one of embodiments A1-A18, wherein the core pharmaceutical substance is methylphenidate.

Embodiment A28. The implantable device of any one of embodiments A1-A18, wherein the core pharmaceutical substance is liraglutide.

Embodiment A29. The implantable device of any one of embodiments A1-A18, wherein the core pharmaceutical substance is doxycycline.

Embodiment A30. The implantable device of any one of embodiments A1-A18, wherein the core pharmaceutical substance is proguanil.

Embodiment A31. The implantable device of any one of embodiments A1-A18, wherein the core pharmaceutical substance is atovaquone.

Embodiment A32. The implantable device of any one of embodiments A1-A18, wherein the core pharmaceutical substance is a combination of proguanil and atovaquone.

Embodiment A33. The implantable device of any one of embodiments A1-A18, wherein the core pharmaceutical substance is nalmefene.

Embodiment A34. The implantable device of any one of embodiments A1-A33, wherein the core pharmaceutical substance comprises about 1% to about 80% of the core.

Embodiment A35. The implantable device of any one of embodiments A1-A33, wherein the core pharmaceutical substance comprises about 10% to about 80% of the core.

Embodiment A36. The implantable device of any one of embodiments A1-A33, wherein the core pharmaceutical substance comprises about 30% to about 70% of the core.

Embodiment A37. The implantable device of any one of embodiments A1-A33, wherein the core pharmaceutical substance comprises about 50% to about 70% of the core.

Embodiment A38. The implantable device of any one of embodiments A1-A37, wherein the first polymeric material is ethylene vinyl acetate (EVA).

Embodiment A39. The implantable device of any one of embodiments A1-A38, wherein the second polymeric material is ethylene vinyl acetate (EVA).

Embodiment A40. The implantable device of any one of embodiments A1-A39, wherein the implantable device releases the core pharmaceutical substance when implanted in the subject with an initial burst at least 50% lower than the initial burst from a comparison implant without the shell.

Embodiment A41. The implantable device of any one of embodiments A1-A39, wherein the implantable device releases the core pharmaceutical substance when implanted in the subject with an initial burst at least 50% lower than the initial burst from a comparison implant where the shell is replaced with additional core material comprising the first polymeric material and the core pharmaceutical substance.

Embodiment A42. A method of forming an implantable device of any one of embodiments A1-A41, comprising extruding a first composition to form the core, the first composition comprising the first polymeric material and the core pharmaceutical substance; and coating the core with a second composition to form the shell, the second composition comprising the second polymeric material and the porogen material.

Embodiment A43. A method of forming an implantable device of any one of embodiments A1-A41, comprising co-extruding a first composition and a second composition, where the first composition is extruded to form the core, the first composition comprising the first polymeric material and the core pharmaceutical substance; and the co-extruded second composition forming the shell around the core, the second composition comprising the second polymeric material and the porogen material.

Embodiment A44. The implantable device of any one of embodiments 1-30 or embodiments A1-41, or the method of any one of embodiments 31-71 or A42-43, wherein the porogenic material is not a pharmaceutically active substance or a drug.

Embodiment A45. The implantable device of any one of embodiments 1-30 or embodiments A1-41, or the method of any one of embodiments 31-71 or A42-43, wherein the porogenic material is not a pharmaceutically active substance or a drug for treating the disease or condition which the device or method is intended to treat.

EXAMPLES

The following examples are intended to illustrate the invention, and are not intended to limit the invention to the embodiments exemplified.

Example 1

Testing Implants in Canines

Implants were prepared by co-extrusion as described above and tested in two groups of dogs, with a third group of dogs serving as control. Each Group 1 dog (n=3) received three implants (30% ethyl cellulose shell/60% $T_3$ core; 26×2.4 mm; 75.8 mg $T_3$), and were followed for about 8 months, including one week after removal of the implants. Each Group 2 dog (n=3) received three $T_3$ implants (60% ethyl cellulose shell/60% $T_3$ core) on day 1, three additional $T_3$ implants on day 87, and three additional $T_3$ implants on day 118, for a dose-escalation study. The core of the $T_3$ implants was about 2 mm in diameter, and the shell thickness was about 0.2 mm (twice the shell thickness is added to the core diameter to obtain the 2.4 mm diameter of the $T_3$ implants). Control dogs (n=3) received EVA-based implants containing no thyroid hormones. The first implant was 4 cm in length and 3 mm in diameter; subsequent implants were 6 cm in length and 3 mm in diameter. Implants were washed with ethanol prior to use. $T_3$, $T_4$, and TSH levels were tested by immunoassay.

Figure 2A:
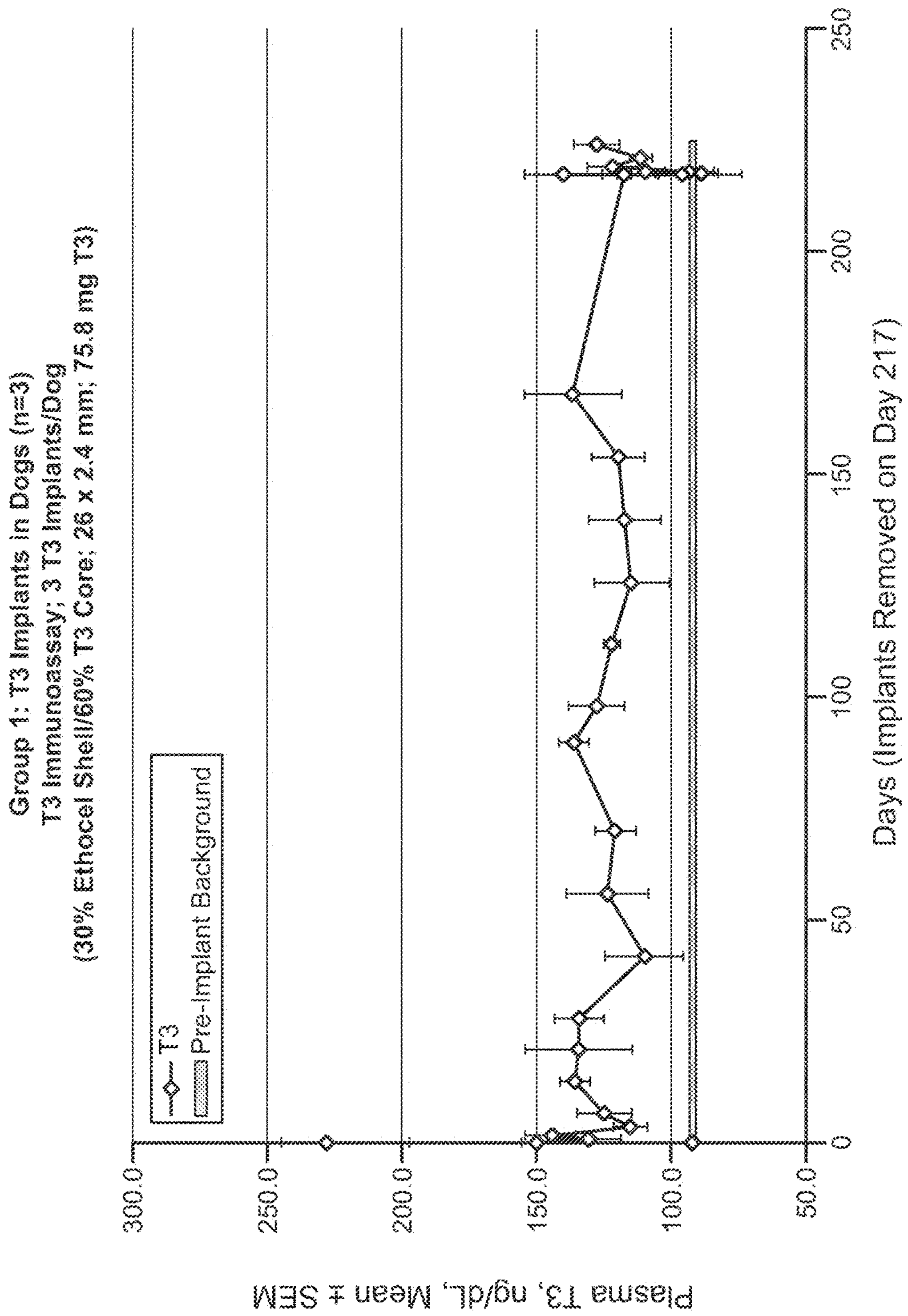
FIG. 2A shows $T_3$ plasma levels (ng/dL) in dogs with $T_3$ implants having 30% ethylcellulose porogen in the shell and 60% $T_3$ in the core.
Figure 2B:
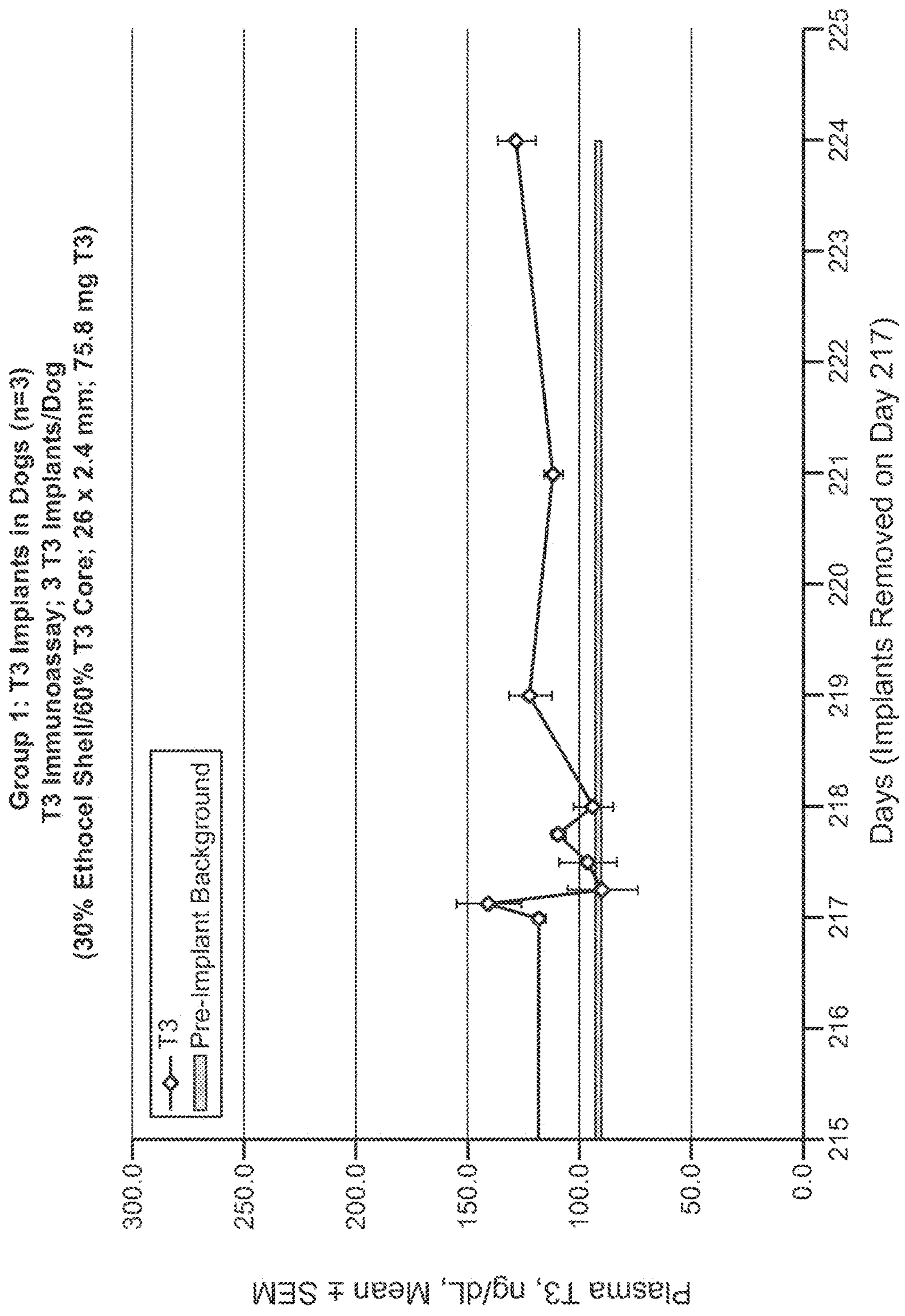
FIG. 2B shows an expanded version of days 215 to 225 from FIG. 2A.

FIG. 2A shows $T_3$ levels in Group 1 dogs. FIG. 2B shows a close-up of $T_3$ levels upon implant removal on Day 217. $T_3$ levels dropped after implants were removed and went back up after 2 days.

Figure 3:
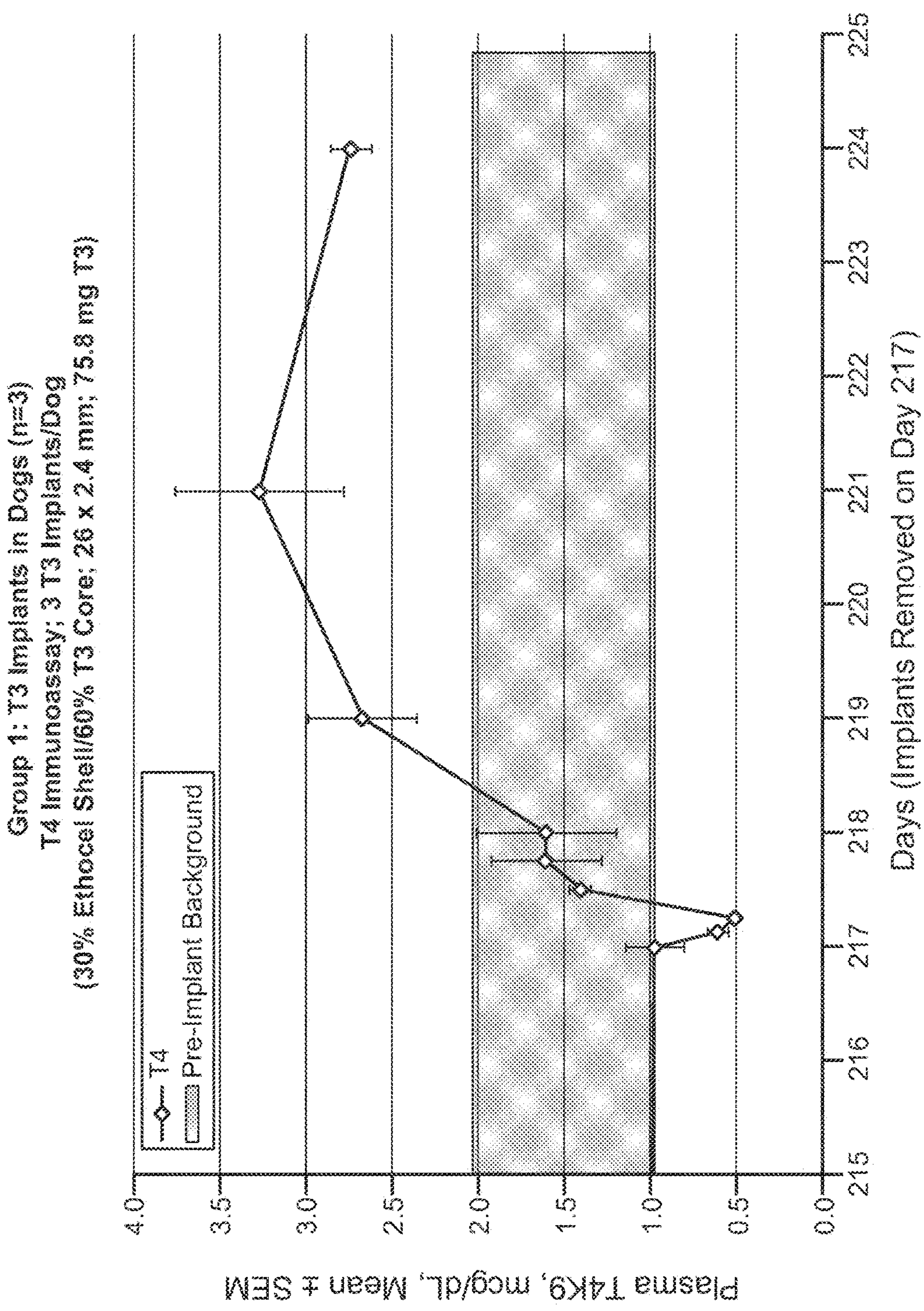
FIG. 3 shows $T_4$ plasma levels (mcg/dL) in dogs before and after removal of $T_3$ implants having 30% ethylcellulose porogen in the shell and 60% $T_3$ in the core.

FIG. 3 shows $T_4$ levels upon Group 1 implant removal on Day 217. $T_4$ levels dropped briefly after implant removal and then rose sharply to peak four days after removal (Day 221). Since $T_4$ is produced only endogenously and is suppressed when there is exogenous $T_3$, this result suggests that the implants were releasing $T_3$ until they were removed (~8 months) when the dogs began to produce excess $T_4$ in response to the drop in $T_3$.

Figure 4A:
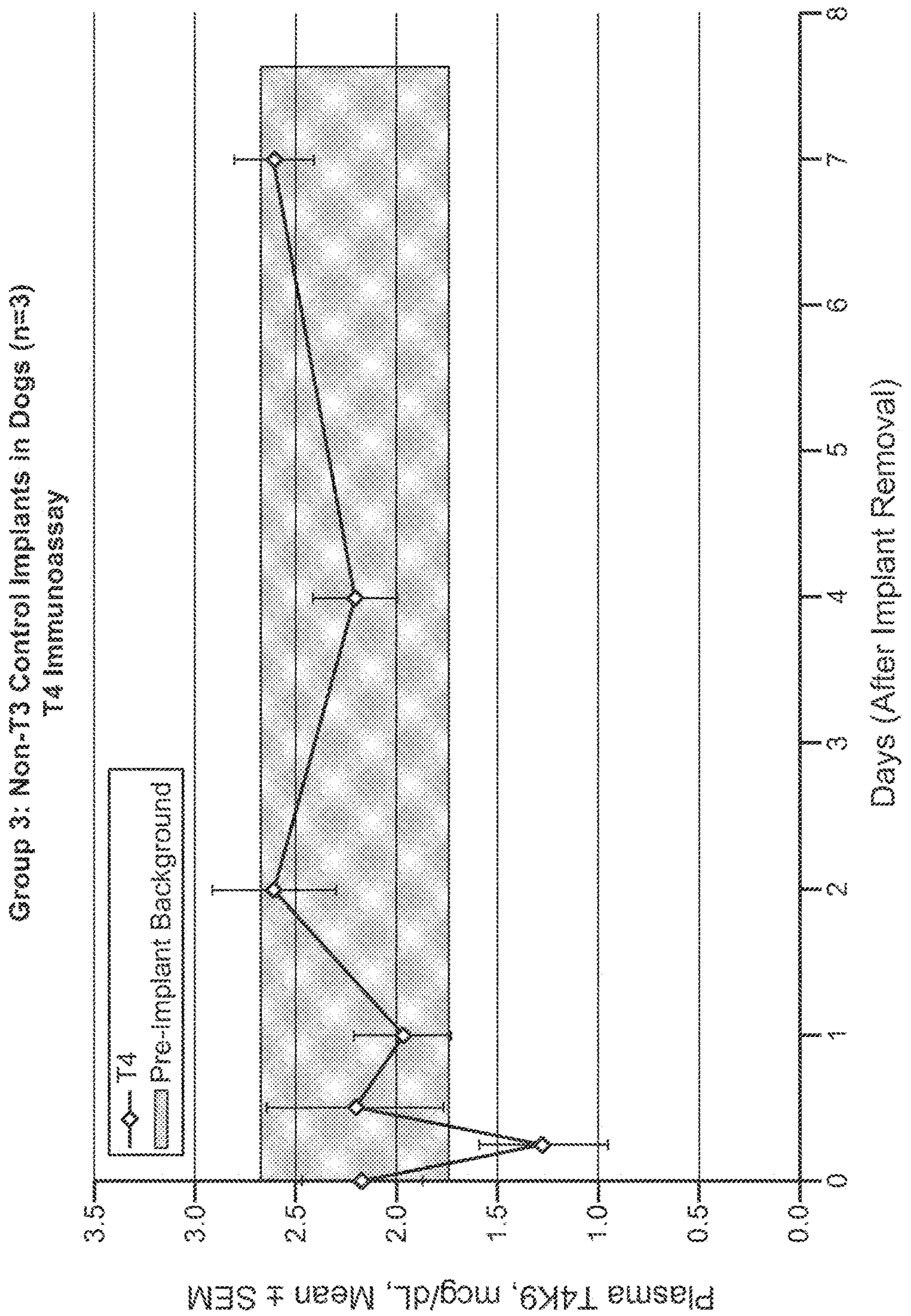
FIG. 4A shows $T_4$ plasma levels (mcg/dL) in control dogs after removal of placebo (non-$T_3$ containing) implants.
Figure 4B:
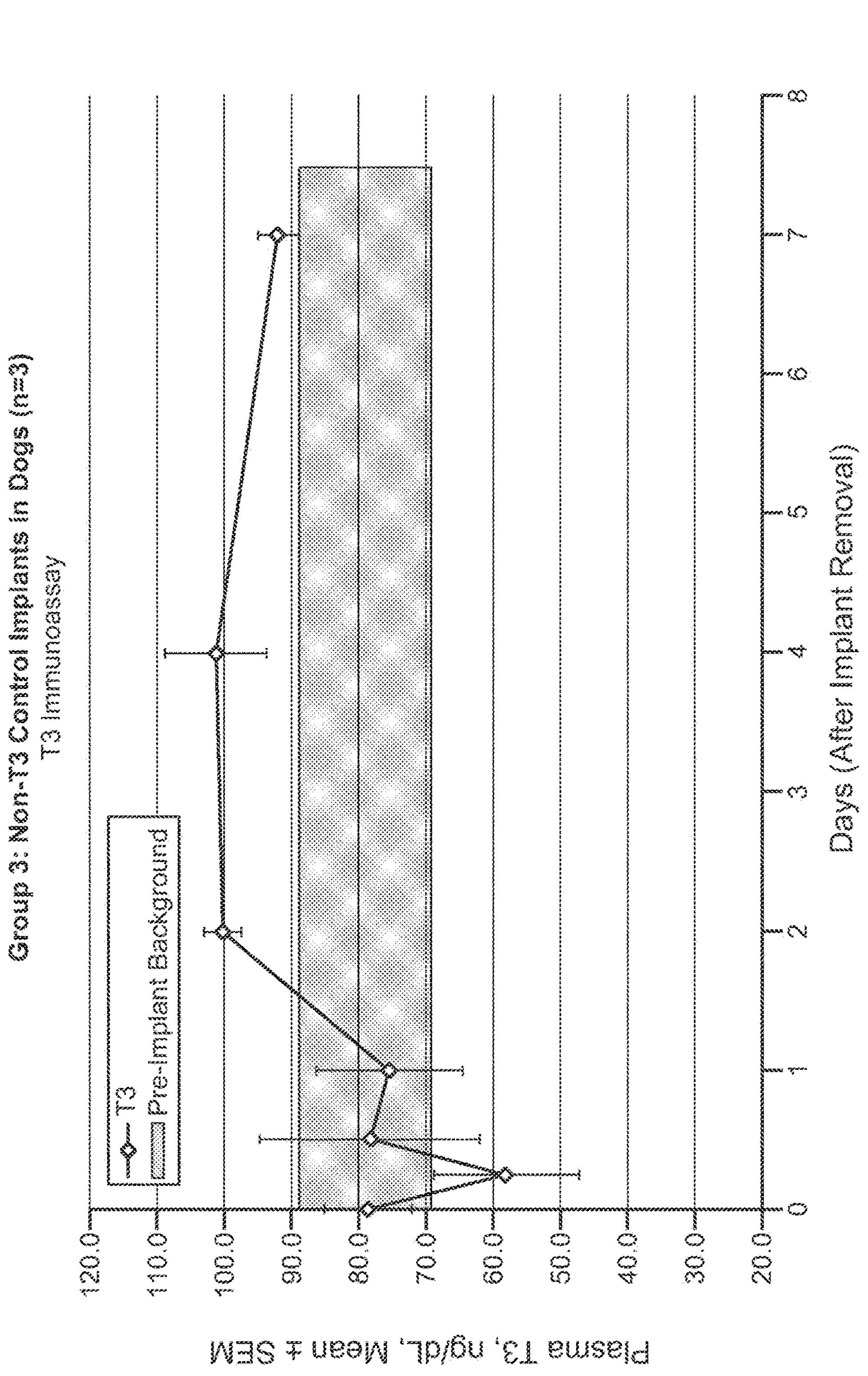
FIG. 4B shows $T_3$ plasma levels (ng/dL) in control dogs after removal of placebo (non-$T_3$ containing) implants.
Figure 4C:
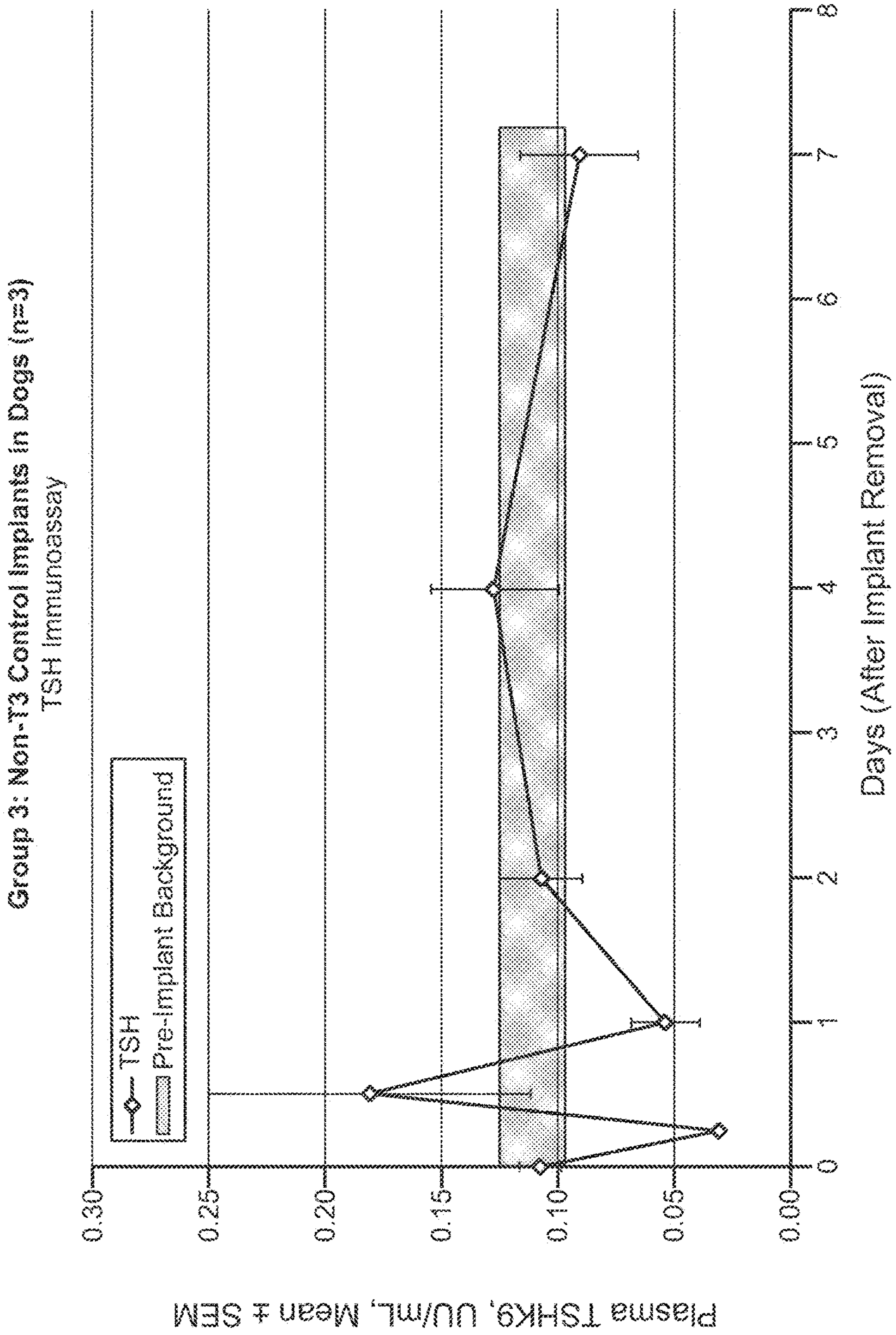
FIG. 4C shows TSH plasma levels in control dogs after removal of placebo (non-$T_3$ containing) implants.

FIG. 4A shows $T_4$ levels upon non-T3 implant removal in the control dogs. FIG. 4B shows $T_3$ levels upon non-T3 implant removal in the control dogs. FIG. 4C shows TSH levels upon non-T3 implant removal in the control dogs. No noticeable effect on $T_3$, TSH or $T_4$ levels were observed after the control non-T3 implants were removed.

Figure 5:
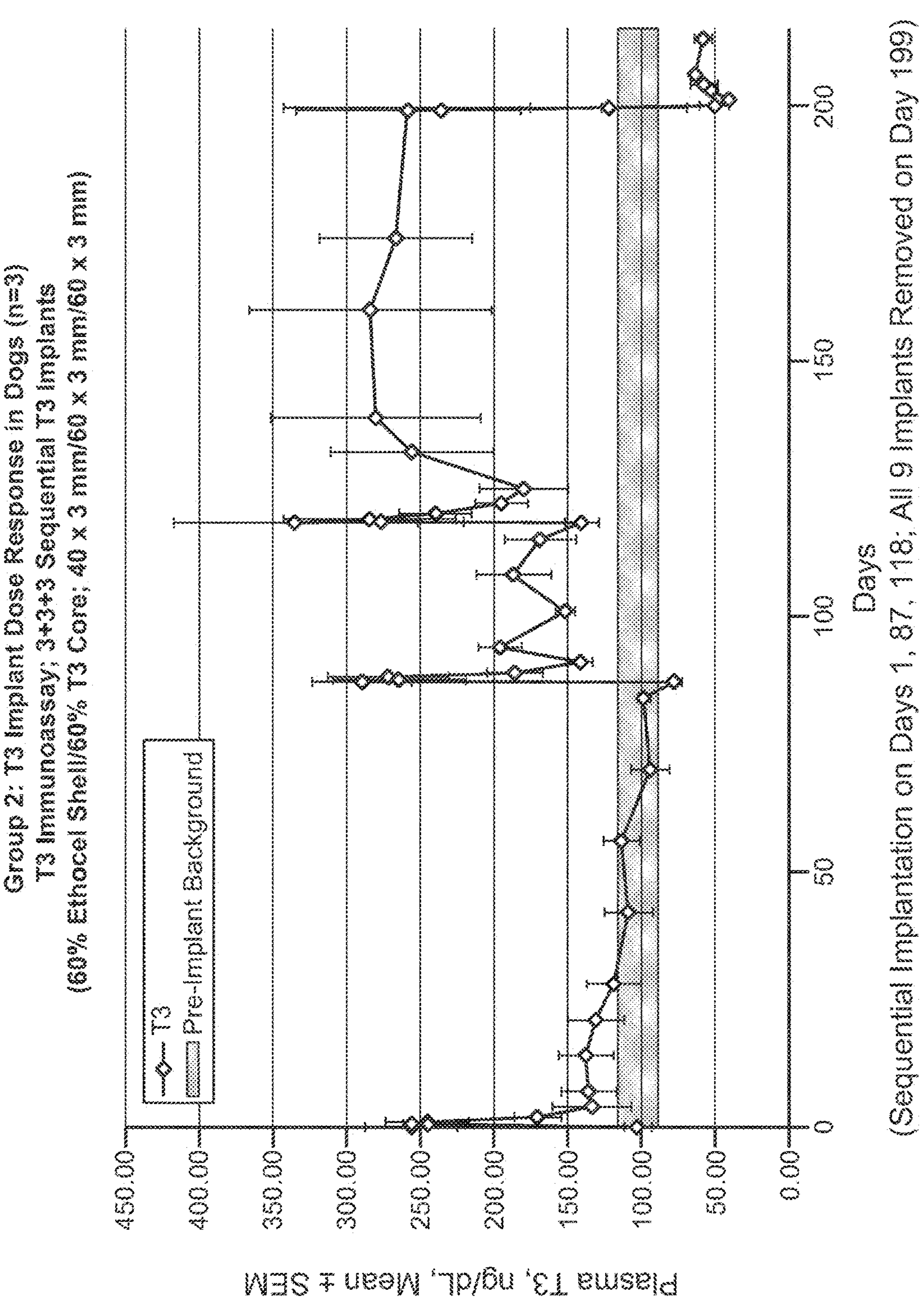
FIG. 5 shows $T_3$ plasma levels (ng/dL) in dogs with a stepwise dose increase in $T_3$ implants having 60% ethylcellulose porogen in the shell and 60% $T_3$ in the core, followed by the removal of all T3 implants.
Figure 6:
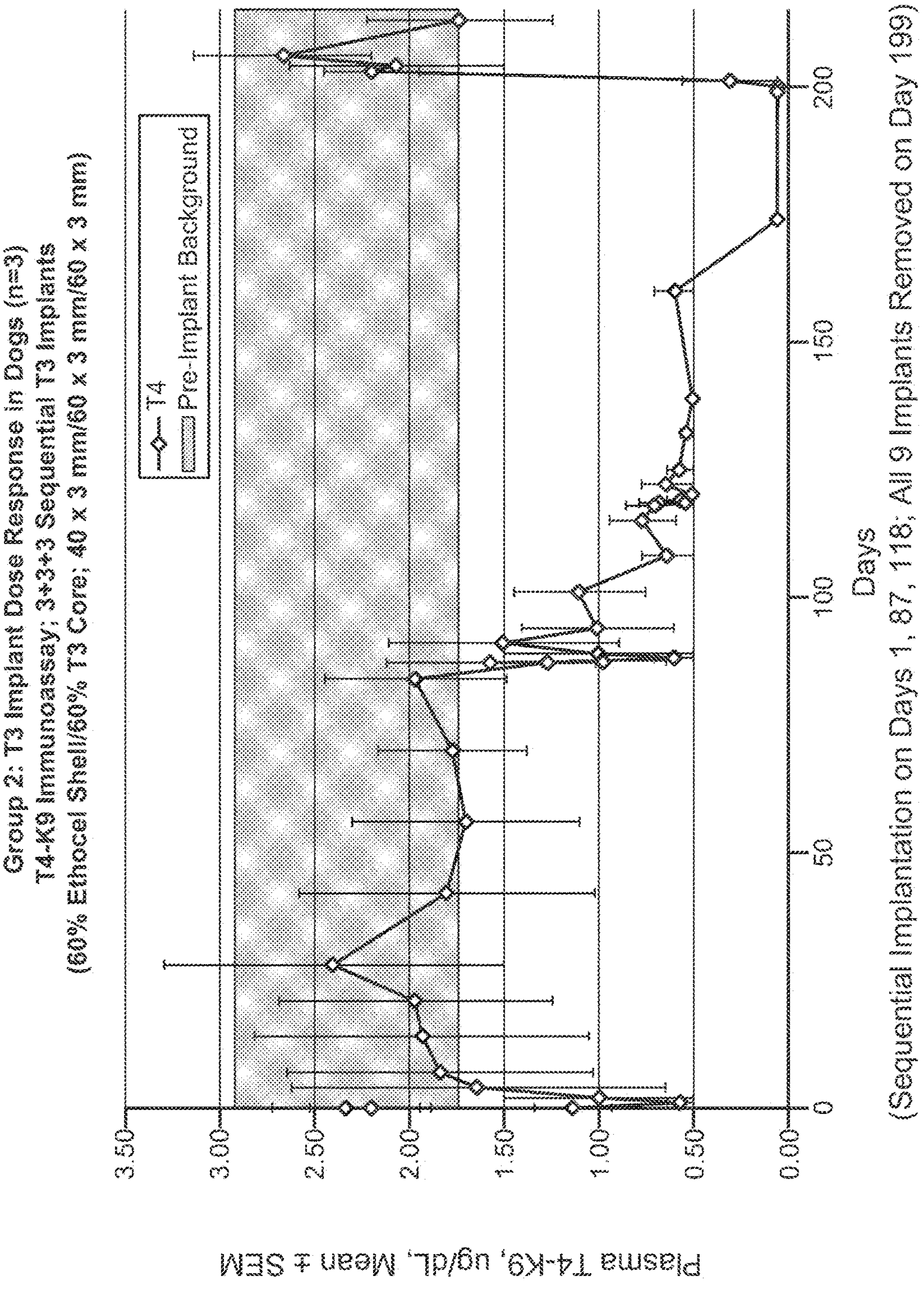
FIG. 6 shows $T_4$ plasma levels (mcg/dL) in dogs with a stepwise dose increase in $T_3$ implants having 60% ethylcellulose porogen in the shell and 60% $T_3$ in the core, followed by the removal of all T3 implants.

FIG. 5 shows $T_3$ levels in Group 2 dogs, implanted with three $T_3$ implants on each of Day 1, Day 87, and Day 118. After each increase in the implantation dose, there was an initial peak followed by steady state release of $T_3$. After all 9 implants were removed, $T_3$ levels dropped sharply. FIG. 6 shows $T_4$ levels in Group 2 dogs. $T_4$ levels dropped after each increase in $T_3$ implant dose. After all 9 implants were removed, $T_4$ levels rose up sharply. TSH levels also dropped with increasing $T_3$ implant dose, and rose after all implants were removed (not shown)

Figure 8:
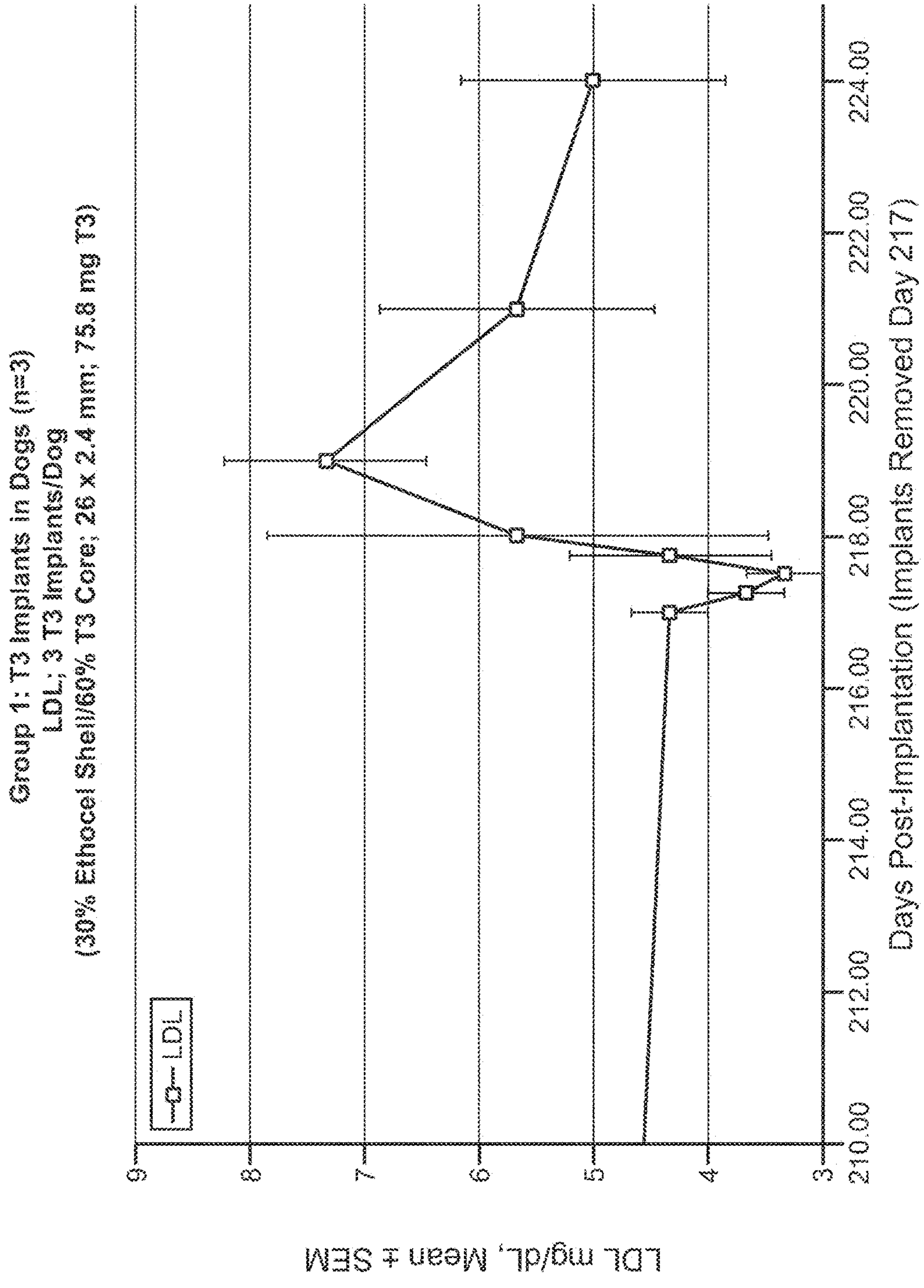
FIG. 8 shows LDL levels in dogs before and after removal of $T_3$ implants having 30% ethylcellulose porogen in the shell and 60% $T_3$ in the core.
Figure 9:
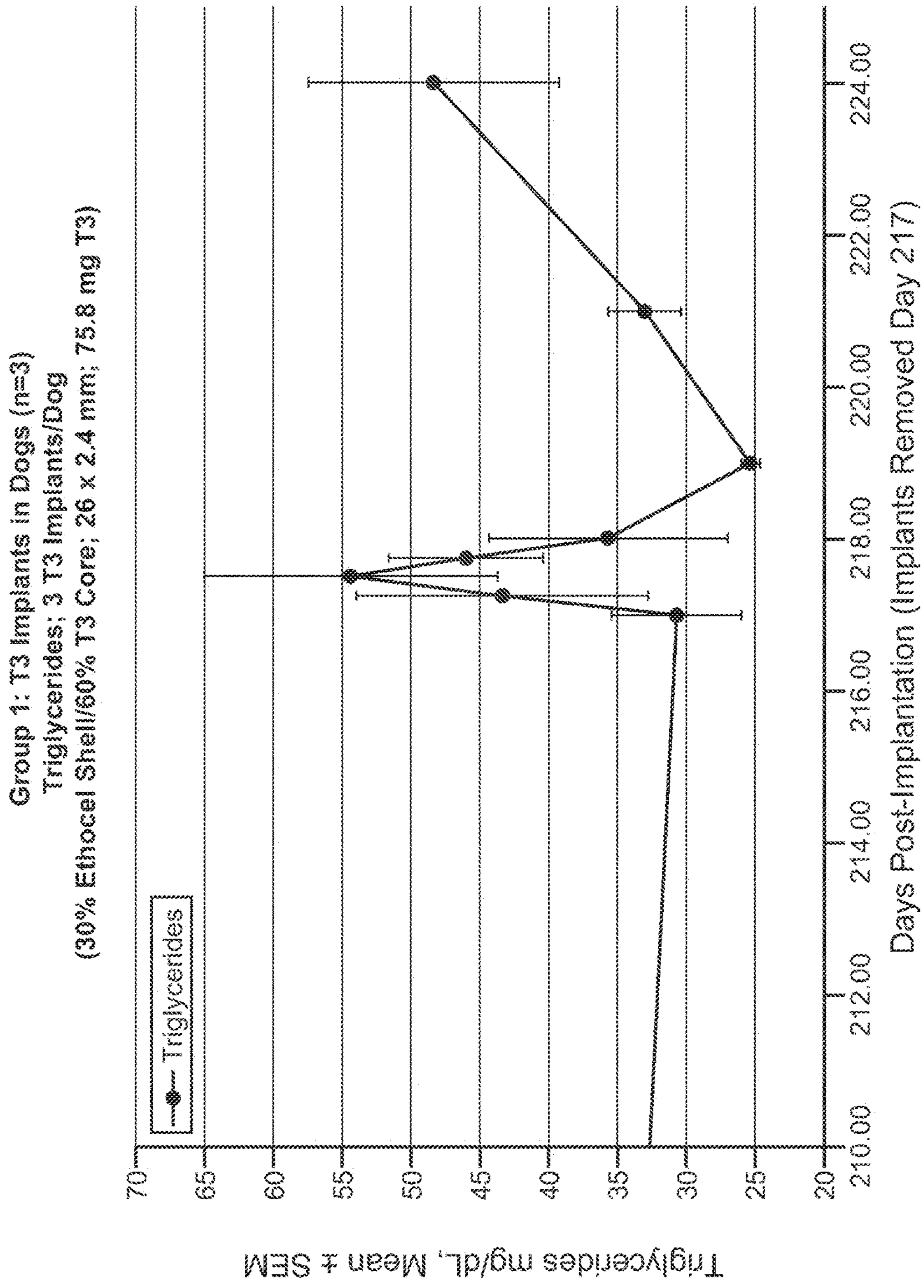
FIG. 9 shows triglyceride levels in dogs before and after removal of $T_3$ implants having 30% ethylcellulose porogen in the shell and 60% $T_3$ in the core.
Figure 10:
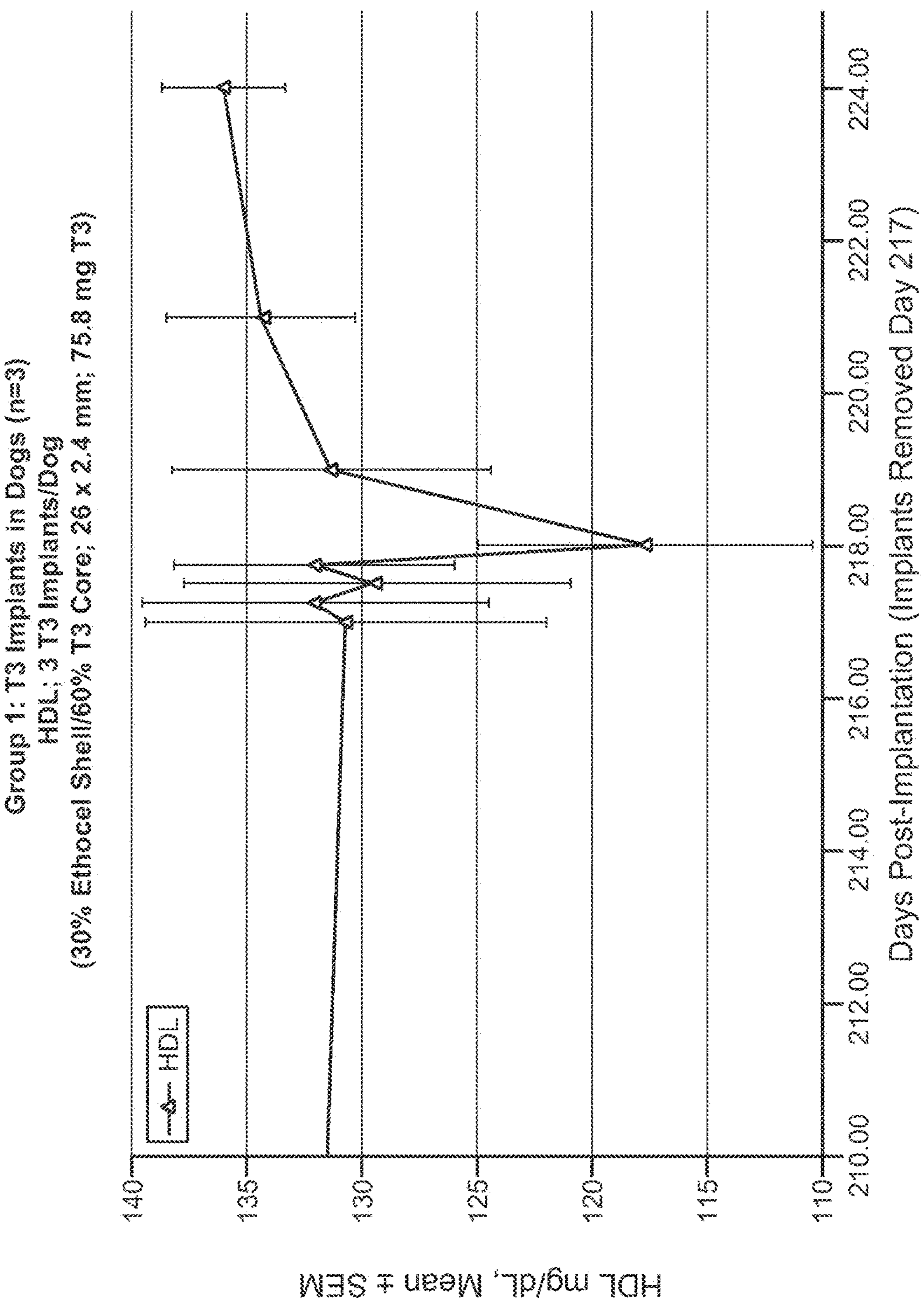
FIG. 10 shows HDL levels in dogs before and after removal of $T_3$ implants having 30% ethylcellulose porogen in the shell and 60% $T_3$ in the core.

$T_3$, but not $T_4$, has been reported to lower LDL and triglycerides in hypothyroid human subjects in a study conducted by the NIH. Celi et al. reported that substitution of L-$T_3$ for L-$T_4$ at equivalent doses (relative to the pituitary) reduced body weight and resulted in greater thyroid hormone action on lipid metabolism (Celi et al., J. Clin. Endocrinol. Metab. (2011), 96(11):3466-74). Accordingly, a lipid panel was run on the Group 1 dogs. FIG. 8 shows LDL levels in Group 1 dogs. Mean LDL levels briefly dropped after removal of the T3 implants, and then rose sharply to peak by day 3 post-removal. FIG. 9 shows triglyceride levels in Group 1 dogs. Mean triglyceride levels rose sharply and peaked a day after the $T_3$ implants were removed, then dropped by day 2 and started to rise again. FIG. 10 shows HDL levels in Group 1 dogs. Mean HDL levels were unaffected the first day after the $T_3$ implants were removed, and then dropped sharply by day 2 and went back up by day 3.

Figure 11:
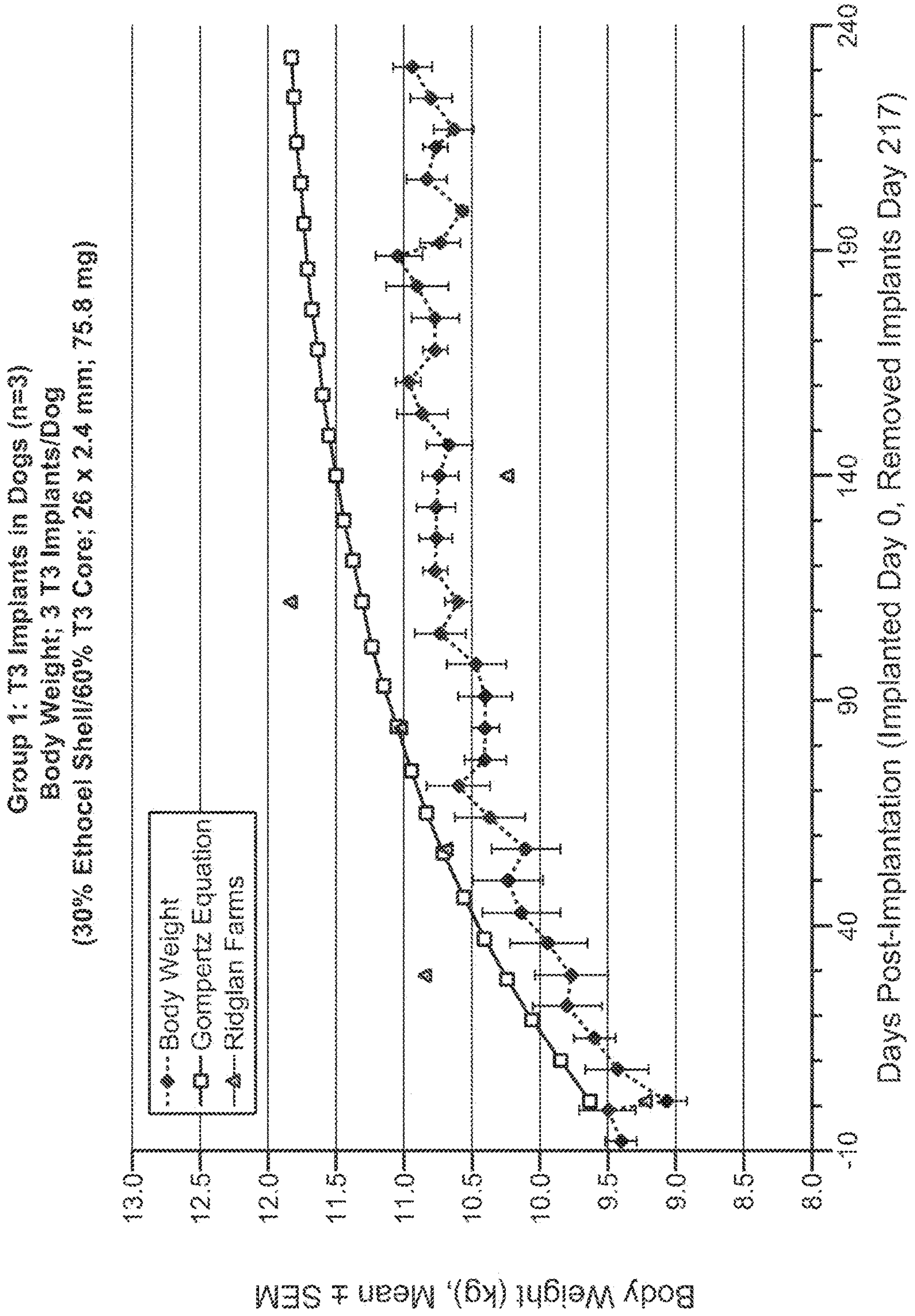
FIG. 11 shows mean observed body weight over time of dogs with $T_3$ implants having 30% ethylcellulose porogen in the shell and 60% $T_3$ in the core versus the predicted body weight over time of untreated dogs.

FIG. 11 shows mean body weight of Group 1 dogs. Mean body weight over time in dogs receiving T3 implants trailed the simulated normal body weight growth curve for beagle dogs derived by the Gompertz equation (Helmsmüller et al. BMC Veterinary Research 2013, 9:203):

$$m_t = m_{max}\exp(-\exp^{[-(t-c)/b]})$$

where $m_t$ is mass at time t, $m_{max}$ is mature body mass, b is proportional to duration of growth, c is the age at point of inflection (i.e., 36.8% of mature body mass) and t is age in weeks. A few recorded mean body weights over time were also obtained from the animal supplier (Ridglan Farms) who noted that body weight values for some beagle dog ages carry the caveat that "due to sales, there are fewer dogs to weigh as the age increases," which may account for the high variability in mean body weights over time reported by Ridglan Farms.

Example 2

Testing T3 Implants in Thyroidectomized Rats

Administration of exogenous $T_3$ results in a decrease in production of endogenous $T_3$ by the thyroid. In order to get around the issue of endogenous $T_3$ confounding the analysis of $T_3$ release from implants, a thyroidectomized rat model with low background $T_3$ was employed.

Figure 7:
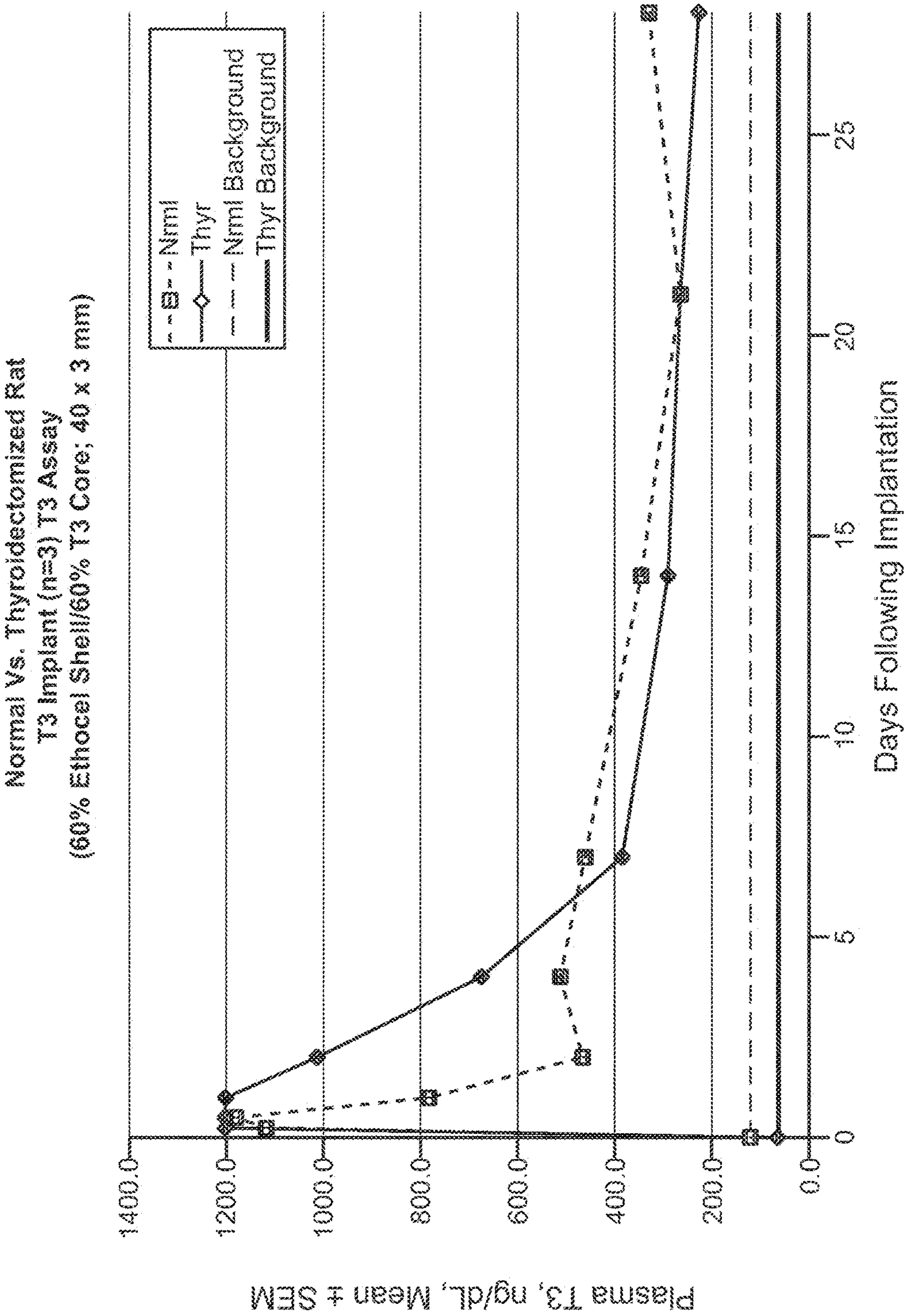
FIG. 7 shows $T_3$ plasma levels (ng/dL) in thyroidectomized rats versus normal rats, respectively bearing $T_3$ implants having 60% ethylcellulose porogen in the shell and 60% $T_3$ in the core. The data for normal rats in FIG. 7 is also shown in FIG. 12A and FIG. 12B, using different units.

Each thyroidectomized rat (n=3) received one $T_3$ implant (60% Ethocel Shell/60% $T_3$ Core; 40×3 mm) (ETHOCEL is a registered trademark of the Dow Chemical Company, Midland, Michigan, United States, for ethyl cellulose polymer). The results are shown in FIG. 7, with comparison to normal rats. $T_3$ release from $T_3$ implants in thyroidectomized rats parallel that seen for these implants in normal rats. The assay upper limits of quantitation were capped at 1200 ng/dL. Implants were washed with ethanol prior to use.

Figure 12A:
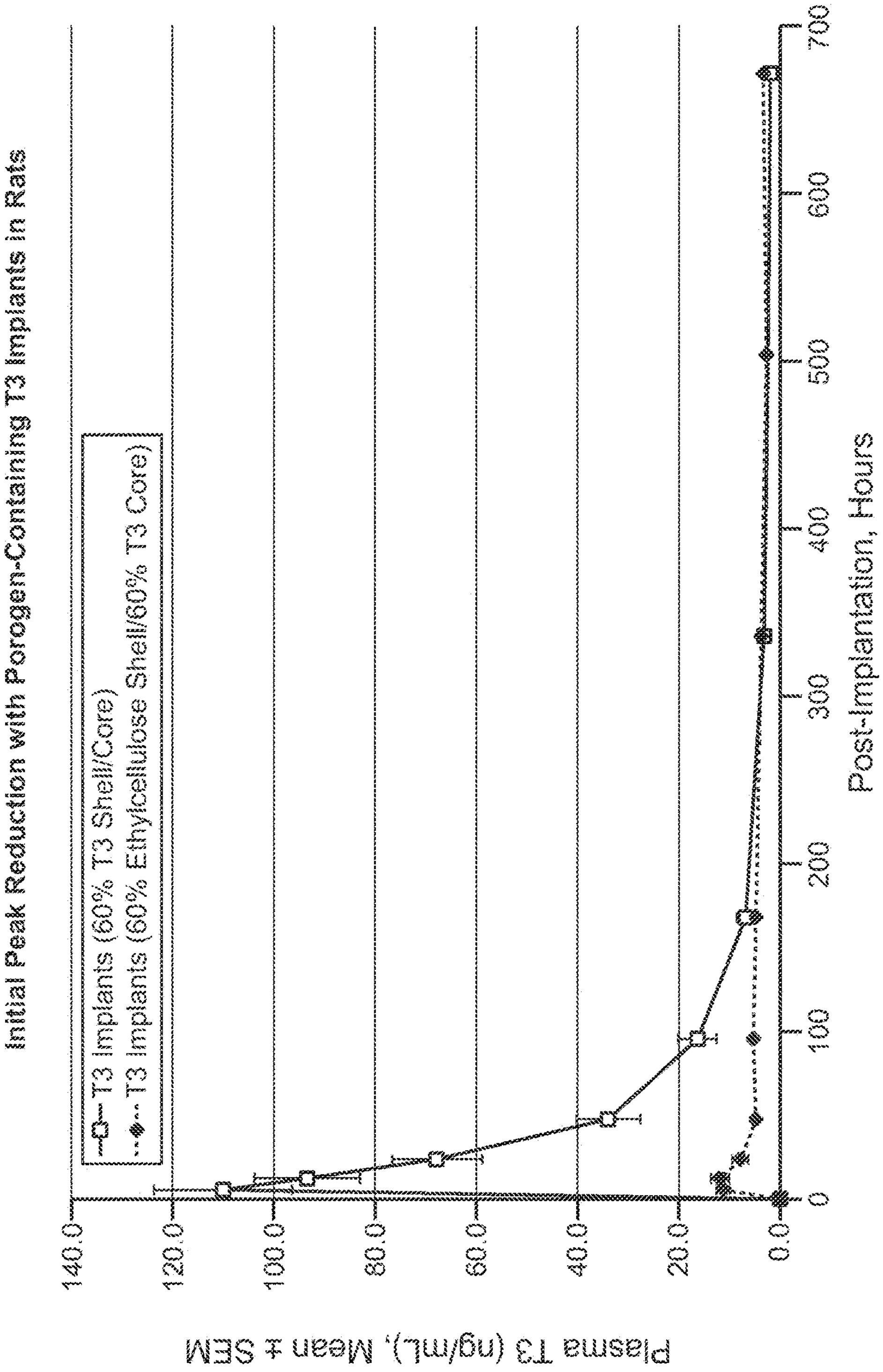
FIG. 12A shows the reduction of burst release upon initial implantation of a drug-containing core/porogen shell implant, as compared to an implant where both the core and the shell contain drug. A linear scale is used for the Y-axis, which uses units of ng/ml. The data for the drug-containing core/porogen shell implant is also shown in FIG. 7 using different units.
Figure 12B:
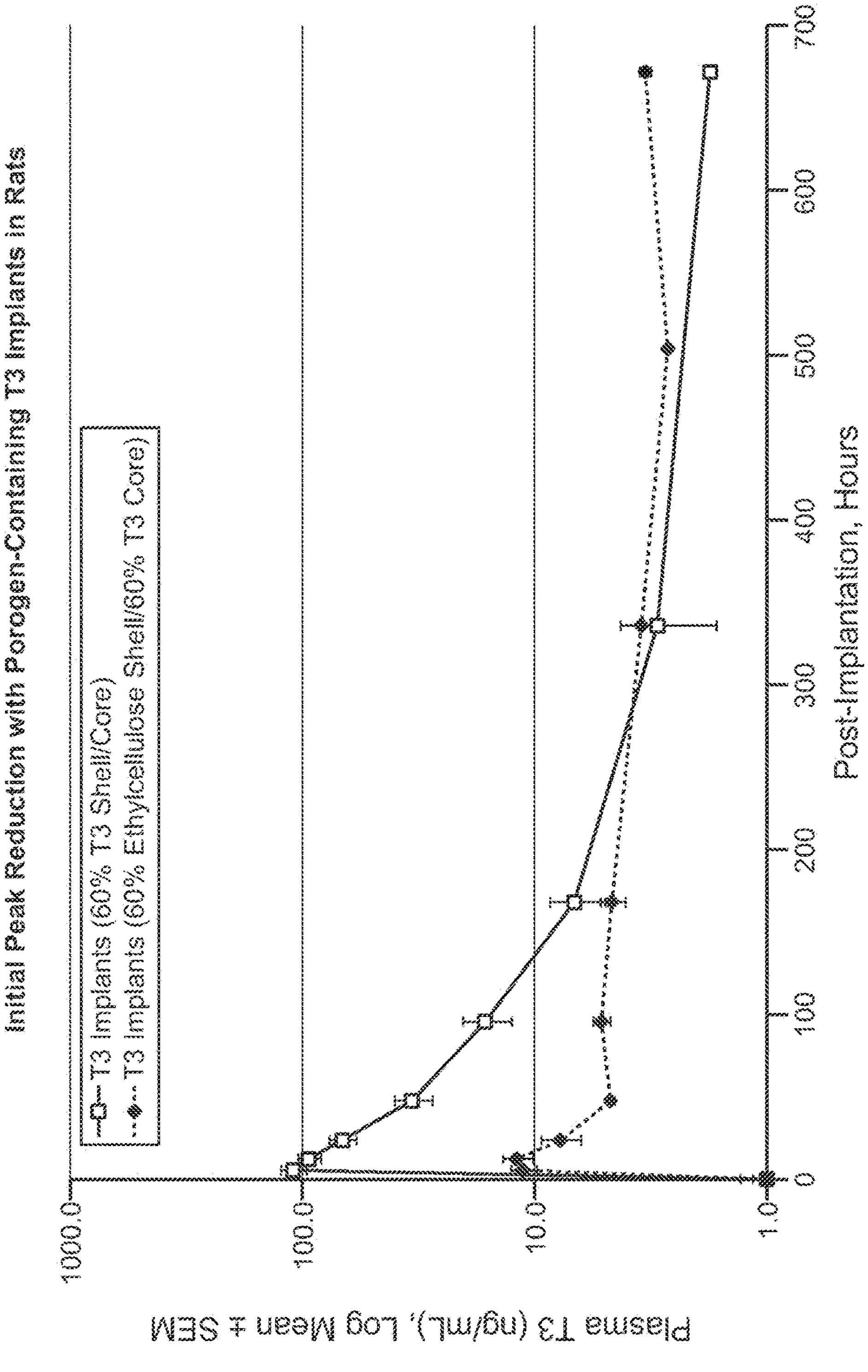
FIG. 12B shows the same data as FIG. 12A, using a logarithmic scale for the Y-axis (ng/ml). The data for the drug-containing core/porogen shell implant is also shown in FIG. 7 using different units.

The data for the normal rats receiving the 60% Ethocel Shell/60% $T_3$ Core implant is also shown in FIG. 12A and FIG. 12B, in comparison to normal rats receiving a 60% $T_3$ Shell/Core implant.

Example 3

Ropinirole Implants in Dogs

Implants were prepared containing ropinirole. Implants with no shell ("core-only" implant) were prepared with 60% ropinirole in EVA, which were 2.4 mm in diameter and 26 mm in length. Two different sets of implants with shells were prepared. One set of shelled implants was prepared which was 40 mm long and 3 mm in diameter, having the same 2.4-mm-diameter 60% ropinirole in EVA core, and with a 0.3 mm-thick shell having 10% ETHOCEL in an EVA shell (twice the shell thickness is added to the core diameter to obtain the 3 mm diameter of these implants). The second set of shelled implants was similar, but was 60 mm long instead of 40 mm long. The implants were washed with ethanol prior to subdermal implantation. Three groups of male beagle dogs were used, with three dogs in each group. Three dogs received two implants each of the no-shell, core-only implant; three dogs received two implants each of the 40-mm-long implants with shell, and three dogs received two implants each of the 60-mm-long implants with shell.

Figure 13A:
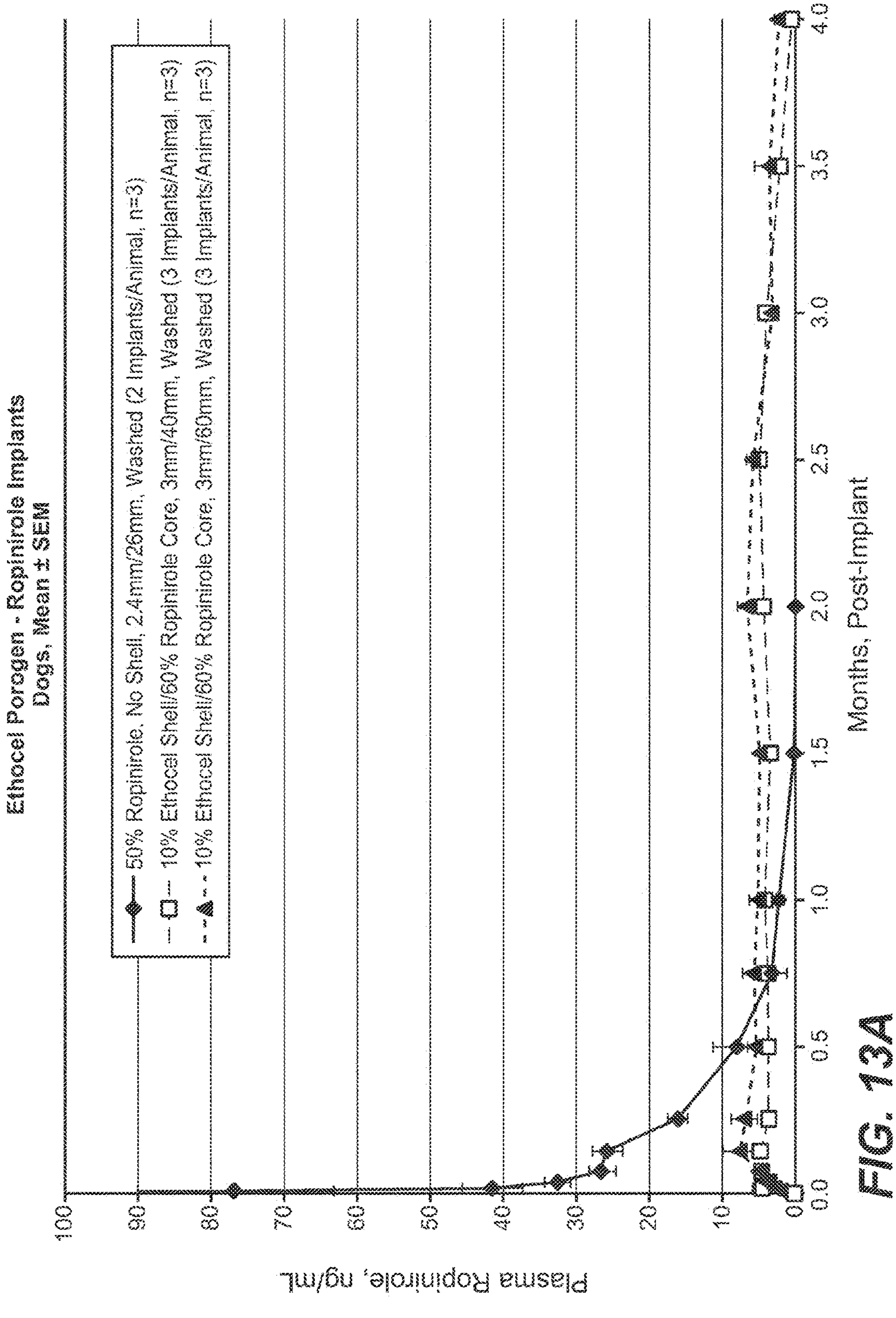
FIG. 13A shows the reduction of burst release upon initial implantation of a ropinirole-containing core/porogen shell implant, as compared to the core of the implant without the shell. A linear scale is used for the Y-axis, which uses units of ng/mL.
Figure 13B:
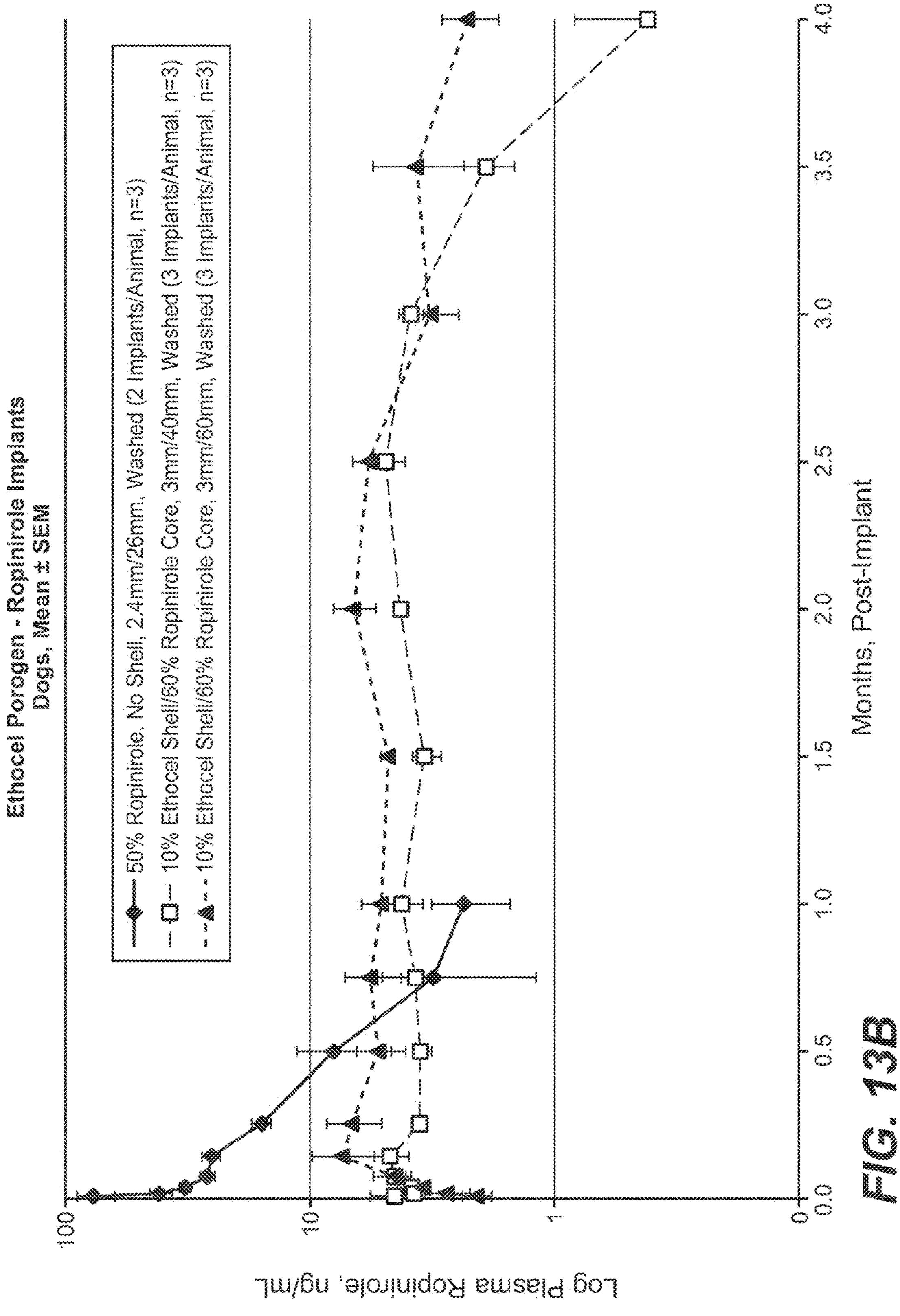
FIG. 13B shows the same data as FIG. 13A, using a logarithmic scale for the Y-axis (ng/mL).

Plasma levels of ropinirole in the animals is shown in FIG. 13A (Y-axis in linear scale) and FIG. 13B (Y-axis in log scale). Error bars indicate standard error of the mean (SEM). As can be readily seen, the implants with no shell had significant burst release, while the implants with porogen-containing shells had burst release reduced by nearly an order of magnitude, and could be considered as having no burst release. The implants with no shell had a highly variable release over two months, while the resulting plasma levels from the implants with porogen-containing shell had much more consistent plasma levels extending for three months, and had non-zero plasma levels at least as far out as 3.5 months.

Example 4

Benzoic Acid and Citric Acid as Shell Porogens

Citric acid and benzoic acid were spray dried from ethanol solution (10% w/v solids) using a ProCepT model 4M8 system. The citric acid was collected in a single fraction in about 65% yield, while the benzoic acid was collected in two fractions with a total yield of around 55%. The powders were characterized for particle size and morphology using an Olympus BX60 optical microscope. The spray drying operation resulted in fine, flowable powders for both citric and benzoic acid. Overall, the citric acid exhibited a smaller particle size (10-20 μm) than the benzoic acid (30-150 μm). The two preparations of benzoic acid differed primarily by the preponderance of ribbon-like particles in the second fraction. The citric acid powder blend was appreciably more dense than the benzoic acid powder blends, and the latter required more careful sweeping of the feeder hopper to promote conveyance. However, the ultimate extrusion, molding, and physical handling characteristics were similar between the blends.

The spray-dried powders were blended with milled EVA polymer with a porogen loading of 60% by weight. Three separate blends were prepared, respectively, containing citric acid, a first preparation of benzoic acid, or a second preparation of benzoic acid. A total of 10-15 g of each blend was prepared and extruded. Neat EVA was used to purge the extruder between the citric and benzoic acid runs.

The porogen formulations were extruded at a barrel temperature setting of 85±5° C. The blended powders were hand fed into the extruder. The molten product exited directly from the extruder's 3 mm orifice (i.e., no external nozzle was applied), and the extruded filaments were collected on a motorized conveyor belt (Dorner 2200).

Extruded filaments were hand-cut into ~5 cm segments and pressed into sheets using a heated (100° C.) Carver hydraulic press equipped with aluminum shims (0.02" thick). Both sides of the sheets were protected with PET release film that was removed after cooling. The sheets, nominally 0.45 mm thick, were then cut into 2×2 cm square coupons. These were loaded into jars and soaked overnight in absolute ethanol, which was added in a proportion of 20 mL/g.

After soaking, the soak solution was drained, and the coupons and containers were rinsed with fresh ethanol. After rinsing, the coupons were dried under vacuum in their original containers. Dry weights were recorded, and representative coupons were sectioned for imaging in the Zeiss EVO-50 environmental SEM.

The weight loss after drying of the extruded, pressed, and washed EVA coupons indicated near-quantitative elimination of the porogens (see Table 1), and the washed surfaces appeared free from particulate. The observed variation in weight loss likely reflects differences in the local the blend homogeneity.

TABLE 1

Weight loss behaviors for organic acid-loaded EVA coupons.

| | EVA/Citric Acid | EVA/Benzoic Acid (first preparation) | EVA/Benzoic Acid (second preparation) |
|---|---|---|---|
| Porogen Loading as Formulated by Weight | 60.0% | 60.0% | 60.0% |
| Net Weight Before Washing (g) | 5.211 | 3.683 | 4.788 |
| Net Weight After Wash & Dry (g) | 2.160 | 1.381 | 1.847 |
| Percent Weight Lost to Washing | 58.5% | 62.5% | 61.4% |

Figure 14:
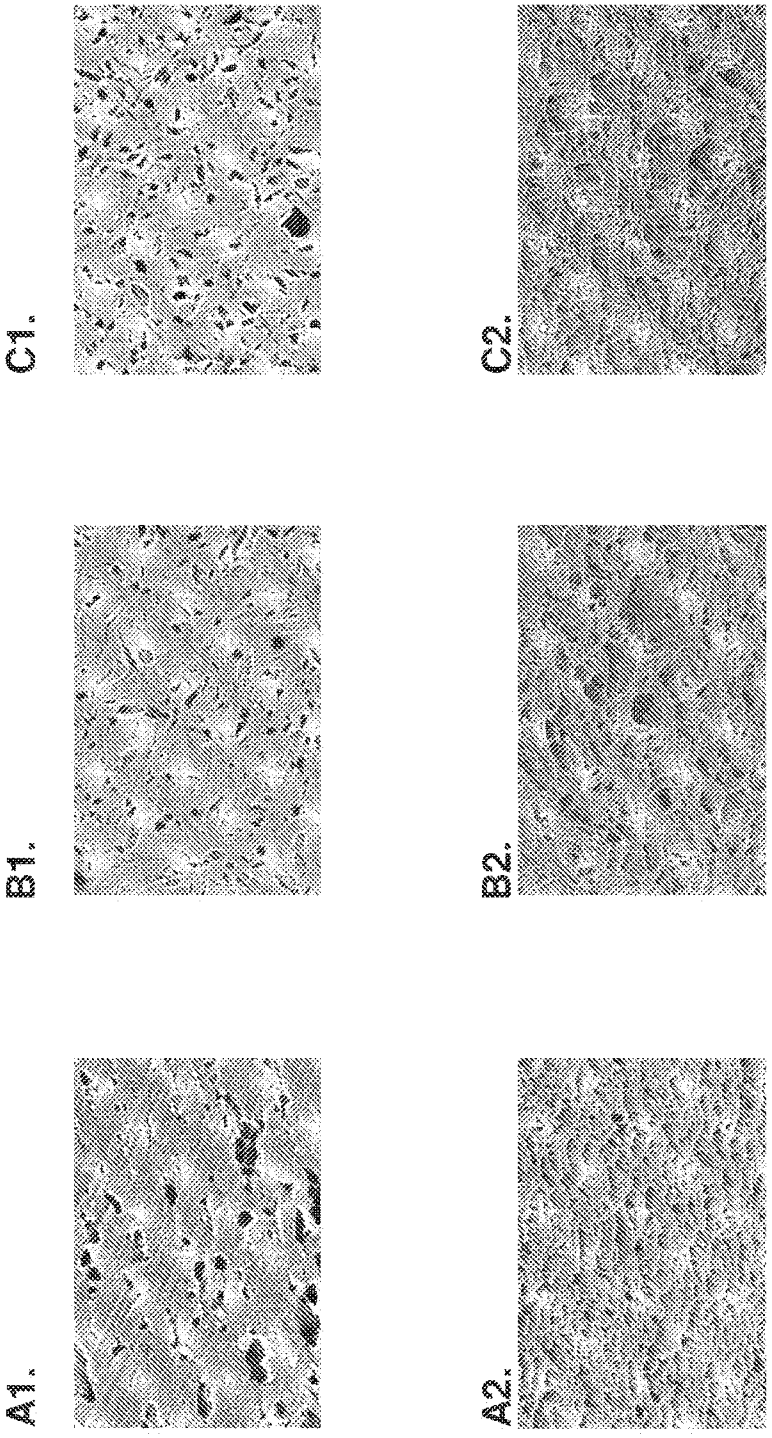
FIG. 14 shows environmental scanning electron micrographs of washed EVA sheets viewed from the top (upper row, panels A1, B1, and C1) and cross-sectional (lower row, panels A2, B2, and C2) perspectives, showing voids (pores) after washing. Panels A1 and A2 used citric acid as porogen. Panels B1 and B2 used benzoic acid as a porogen. Panels C1 and C2 used a different preparation of benzoic acid as a porogen. Each panel shows an approximately 685 micrometer-wide view of the samples.

FIG. 14 shows environmental scanning electron micrographs of washed EVA sheets viewed from the top (upper row, panels A1, B1, and C1) and cross-sectional (lower row, panels A2, B2, and C2) perspectives, showing voids (pores) after washing. Panels A1 and A2 used citric acid as porogen. Panels B1 and B2 used benzoic acid as a porogen. Panels C1 and C2 used a different preparation of benzoic acid as a porogen. Each panel shows an approximately 685 micrometer-wide view of the samples.

All three test groups exhibited highly interconnected porosity following the extrusion, molding, and washing operations. The surface pore distribution was more uniform for the benzoic acid groups, while the cross-sectional pore size distribution was smaller and more uniform throughout the citric acid sample. Given the lower bulk density of the benzoic acid powder blends, more air was likely introduced during the extrusion of those samples. No distinguishing features were evident between the two different benzoic acid samples following washing.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entirety.

The invention claimed is:

1. An implantable device for delivery of a pharmaceutical substance comprising:

a core comprising a first polymeric material including ethylene vinyl acetate and a core pharmaceutical substance; and a shell comprising ethylene vinyl acetate and a porogen material comprising ethyl cellulose; wherein the porogen material comprises particles with a mean diameter between 1 micrometer and 300 micrometers; wherein the implantable device has reduced burst release as compared to a comparison device made entirely of the first polymeric material and the core pharmaceutical substance.

2. The implantable device of claim 1, wherein the shell is a non-medicated layer.

3. The implantable device of claim 1, wherein the shell further comprises a shell pharmaceutical substance.

4. The implantable device of claim 3, wherein the shell pharmaceutical substance comprises one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, doxycycline, proguanil, atovaquone, a combination of proguanil and atovaquone, and nalmefene.

5. The implantable device of claim 3, wherein the shell pharmaceutical substance comprises ropinirole or triiodothyronine.

6. The implantable device of claim 3, wherein the shell pharmaceutical substance comprises about 1 wt % to about 40 wt % of the outer layer.

7. The implantable device of claim 1, wherein the shell comprises about 1 wt % to about 80 wt % porogen material.

8. The implantable device of claim 7, wherein said implantable device further comprises a reinforcing member inside the core.

9. The implantable device of claim 1, wherein the porogen material further comprises a material selected from the group consisting of a hydroxyalkyl cellulose, methylcellulose, hydroxymethylcellulose, a fatty acid, stearic acid, palmitic acid, myristic acid, linoleic acid, a biocompatible salt, sodium chloride, calcium chloride, and sodium phosphate.

10. The implantable device of claim 1, wherein the porogen material dissolves or dissociates from the shell upon washing the implantable device.

11. The implantable device of claim 1, wherein the first polymeric material further comprises one or more materials selected from the group consisting of polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, silicone, acrylonitrile butadiene styrene resins, acrylic polymers and copolymers, acrylonitrile-styrene copolymers, alkyd resins, copolymers of vinyl monomers with each other and olefins, ethylene-methyl methacrylate copolymers, epoxy resins, ethylene vinyl alcohol copolymer, poly(glyceryl sebacate), poly(glycolic acid-co-trimethylene carbonate), poly(hydroxybutyrate-co-valerate), poly(hydroxyvalerate), poly (lactide-co-glycolide), poly(propylene fumarate), poly(trimethylene carbonate), polyacrylonitrile, polyamides, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene fluoride (PVDF), poly(vinylidene-co-hexafluoropropylene) (PVDF-co-HFP), polyvinylidene chloride, rayon, rayon-triacetate, silicones, vinyl halide polymers and copolymers, polyvinyl chloride, and copolymers of these polymers with poly(ethylene glycol) (PEG).

12. The implantable device of claim 1, wherein the implantable device is substantially rod-shaped, wherein the implantable device has a diameter of about 1 mm to about 8 mm, and wherein the implantable device has a length of about 10 mm to about 80 mm.

13. The implantable device of claim 12, wherein the implantable device is capped at one end, or at both ends, of the implantable device.

14. The implantable device of claim 1, wherein the core pharmaceutical substance comprises one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, doxycycline, proguanil, atovaquone, a combination of proguanil and atovaquone, and nalmefene.

15. The implantable device of claim 1, wherein the core pharmaceutical substance comprises ropinirole or triiodothyronine.

16. The implantable device of claim 1, wherein the core pharmaceutical substance comprises about 1 wt % to about 80 wt % of the core.

17. A method of forming an implantable device comprising:

extruding a first composition to form a core, the first composition comprising a first polymeric material including ethylene vinyl acetate and a core pharmaceutical substance; and coating the core with a second composition to form a shell, the second composition comprising ethylene vinyl acetate and a porogen material comprising ethyl cellulose, wherein the porogen material comprises particles with a mean diameter between 1 micrometer and 300 micrometers, wherein the implantable device has reduced burst release as compared to a comparison device made entirely of the first polymeric material and the core pharmaceutical substance.

18. The method of claim 17, further comprising washing the implantable device, wherein the implantable device is washed in ethanol, water, or a mixture of ethanol and water, and wherein washing the device dissolves the porogen material or dissociates the porogen material from the implantable device to form a plurality of pores in the shell.

19. The method of claim 17, wherein the second composition is a non-medicated material.

20. The method of claim 17, wherein the second composition further comprises a shell pharmaceutical substance.

21. The method of claim 20, wherein the shell pharmaceutical substance comprises one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, doxycycline, proguanil, atovaquone, a combination of proguanil and atovaquone, and nalmefene.

22. The method of claim 20, wherein the shell pharmaceutical substance comprises ropinirole or triiodothyronine.

23. The method of claim 20, wherein the shell pharmaceutical substance comprises about 1 wt % to about 40 wt % of the second composition.

24. The method of claim 17, wherein the second composition comprises about 1 wt % to about 80 wt % porogen material.

25. The method of claim 17, wherein the porogen material further comprises a material selected from the group consisting of a hydroxyalkyl cellulose, methylcellulose, hydroxymethylcellulose, a fatty acid, stearic acid, palmitic acid, myristic acid, linoleic acid, a biocompatible salt, sodium chloride, calcium chloride, and sodium phosphate.

26. The method of claim 17, wherein the first polymeric material further comprises one or more materials selected from the group consisting of polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, silicone, acrylonitrile butadiene styrene resins, acrylic polymers and copolymers, acrylonitrile-styrene copolymers, alkyd resins, copolymers of vinyl monomers with each other and olefins, ethylene-methyl methacrylate copolymers, epoxy resins, ethylene vinyl alcohol copolymer, poly(glyceryl sebacate), poly(glycolic acid-co-trimethylene carbonate), poly(hydroxybutyrate-co-valerate), poly(hydroxyvalerate), poly(lactide-co-glycolide), poly(propylene fumarate), poly(trimethylene carbonate), polyacrylonitrile, polyamides, polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, polystyrene, polyvinyl esters, polyvinyl acetate, polyvinyl ethers, polyvinyl methyl ether, polyvinylidene fluoride (PVDF), poly(vinylidene-co-hexafluoropropylene) (PVDF-co-HFP), polyvinylidene chloride, rayon, rayon-triacetate, silicones, vinyl halide polymers and copolymers, polyvinyl chloride, and copolymers of these polymers with poly(ethylene glycol) (PEG).

27. The method of claim 17, wherein the implantable device is substantially rod-shaped, wherein the implantable device has a diameter of about 1 mm to about 8 mm, and wherein the implantable device has a length of about 10 mm to about 80 mm.

28. The method of claim 17, further comprising capping the implantable device at one end, or at both ends, of the implantable device.

29. The method of claim 17, wherein the core pharmaceutical substance comprises one or more substances selected from the group consisting of L-thyroxine ($T_4$), L-triiodothyronine ($T_3$), a combination of L-thyroxine ($T_4$) and L-triiodothyronine ($T_3$), ropinirole, tenofovir, emtricitabine, a combination of tenofovir and emtricitabine, bosentan, methylphenidate, liraglutide, doxycycline, proguanil, atovaquone, a combination of proguanil and atovaquone, and nalmefene.

30. The method of claim 17, wherein the core pharmaceutical substance comprises ropinirole or triiodothyronine.

31. The method of claim 17, wherein the core pharmaceutical substance comprises about 1 wt % to about 80 wt % of the first composition.

32. A method of forming an implantable device comprising:

co-extruding a first composition and a second composition, where the first composition is extruded to form a core, the first composition comprising a first polymeric material including ethylene vinyl acetate and a core pharmaceutical substance; and the co-extruded second composition forming a shell around the core, the second composition comprising ethylene vinyl acetate and a porogen material comprising ethyl cellulose, wherein the porogen material comprises particles with a mean diameter between 1 micrometer and 300 micrometers, wherein the implantable device has reduced burst release as compared to a comparison device made entirely of the first polymeric material and the core pharmaceutical substance.

* * * * *